(12) United States Patent
Johnson et al.

(10) Patent No.: US 9,913,731 B2
(45) Date of Patent: *Mar. 13, 2018

(54) EXPANDABLE INTERBODY FUSION DEVICE

(71) Applicant: SPINE WAVE, INC., Shelton, CT (US)

(72) Inventors: Wes Johnson, Eden Prairie, MN (US);
Tyler Lipschultz, San Diego, CA (US);
Larry Wales, Maplewood, MN (US);
Robert Kieval, Minneapolis, MN (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/598,725

(22) Filed: May 18, 2017

(65) Prior Publication Data

US 2017/0252184 A1    Sep. 7, 2017

Related U.S. Application Data

(60) Continuation of application No. 14/628,707, filed on Feb. 23, 2015, now Pat. No. 9,655,743, which is a
(Continued)

(51) Int. Cl.
*A61B 17/70* (2006.01)
*A61F 2/44* (2006.01)
(Continued)

(52) U.S. Cl.
CPC .......... *A61F 2/4455* (2013.01); *A61B 17/025* (2013.01); *A61B 17/66* (2013.01);
(Continued)

(58) Field of Classification Search
CPC ........ A61F 2/4455; A61F 2/44; A61F 2/4425; A61F 2/4611; A61B 17/025; A61B 17/66; A61B 17/8852
(Continued)

(56) References Cited

U.S. PATENT DOCUMENTS 3,486,505 A    12/1969  Morrison
3,867,728 A    2/1975   Stubstad et al.
(Continued)

FOREIGN PATENT DOCUMENTS

EP    0621020    10/1994
FR    2639823    6/1990
(Continued)

OTHER PUBLICATIONS

Barr, John D. MD et al.; Percutaneous Vertebroplasty for Pain Relieve and Spinal Stabilization, SPINE, vol. 25, No. 8, pp. 923-928; 2000.
(Continued)

*Primary Examiner* — Pedro Philogene
*Assistant Examiner* — David C Comstock
(74) *Attorney, Agent, or Firm* — Hoffmann & Baron, LLP

(57) ABSTRACT

An apparatus and method is provided for interbody fusion including distracting, in a given direction, and supporting opposing vertebral bodies. A plurality of wafers are consecutively inserted between the vertebral bodies to create a column of wafers. The column of wafers is oriented between the vertebral bodies so as to expand in the given direction as the wafers are consecutively added to the column.

10 Claims, 21 Drawing Sheets

Related U.S. Application Data continuation of application No. 14/027,421, filed on Sep. 16, 2013, now Pat. No. 8,974,464, which is a continuation of application No. 13/176,830, filed on Jul. 6, 2011, now Pat. No. 8,535,353, which is a continuation of application No. 11/867,746, filed on Oct. 5, 2007, now Pat. No. 8,123,755, which is a division of application No. 10/623,957, filed on Jul. 21, 2003, now Pat. No. 7,311,713, which is a continuation of application No. 09/872,905, filed on Jun. 1, 2001, now Pat. No. 6,595,998.

(60) Provisional application No. 60/274,372, filed on Mar. 8, 2001.

(51) Int. Cl.
| | |
|---|---|
| *A61B 17/88* | (2006.01) |
| *A61F 2/46* | (2006.01) |
| *A61B 17/66* | (2006.01) |
| *A61B 17/02* | (2006.01) |
| *A61F 2/28* | (2006.01) |
| *A61F 2/30* | (2006.01) |

(52) U.S. Cl.
CPC ............ *A61B 17/8852* (2013.01); *A61F 2/44* (2013.01); *A61F 2/442* (2013.01); *A61F 2/4425* (2013.01); *A61F 2/4611* (2013.01); *A61B 17/7097* (2013.01); *A61B 2017/0256* (2013.01); *A61F 2/28* (2013.01); *A61F 2/447* (2013.01); *A61F 2002/304* (2013.01); *A61F 2002/305* (2013.01); *A61F 2002/3008* (2013.01); *A61F 2002/3049* (2013.01); *A61F 2002/30075* (2013.01); *A61F 2002/30237* (2013.01); *A61F 2002/30261* (2013.01); *A61F 2002/30385* (2013.01); *A61F 2002/30387* (2013.01); *A61F 2002/30392* (2013.01); *A61F 2002/30448* (2013.01); *A61F 2002/30449* (2013.01); *A61F 2002/30462* (2013.01); *A61F 2002/30476* (2013.01); *A61F 2002/30599* (2013.01); *A61F 2002/30604* (2013.01); *A61F 2002/30616* (2013.01); *A61F 2002/30772* (2013.01); *A61F 2002/4415* (2013.01); *A61F 2002/4485* (2013.01); *A61F 2002/4627* (2013.01); *A61F 2002/4666* (2013.01); *A61F 2210/0061* (2013.01); *A61F 2220/005* (2013.01); *A61F 2220/0025* (2013.01); *A61F 2220/0075* (2013.01); *A61F 2230/0069* (2013.01); *A61F 2230/0082* (2013.01); *A61F 2250/0063* (2013.01); *A61F 2250/0098* (2013.01); *A61F 2310/00017* (2013.01); *A61F 2310/00023* (2013.01); *A61F 2310/00029* (2013.01); *A61F 2310/00071* (2013.01); *A61F 2310/00203* (2013.01); *A61F 2310/00239* (2013.01); *A61F 2310/00293* (2013.01); *A61F 2310/00353* (2013.01); *A61F 2310/00359* (2013.01); *A61F 2310/00365* (2013.01); *Y10S 606/907* (2013.01); *Y10S 606/912* (2013.01); *Y10S 606/914* (2013.01)

(58) Field of Classification Search
USPC ..... 606/246, 279, 99, 104, 86 A; 623/17.11, 623/17.15, 17.16
See application file for complete search history.

(56) References Cited

U.S. PATENT DOCUMENTS

| | | |
|---|---|---|
| 4,065,817 A | 1/1978 | Branemark et al. |
| 4,274,163 A | 6/1981 | Malcom et al. |
| 4,349,921 A | 9/1982 | Kuntz |
| 4,359,785 A | 11/1982 | Niederer |
| 4,494,535 A | 1/1985 | Haig |
| 4,524,766 A | 6/1985 | Petersen |
| 4,653,487 A | 3/1987 | Maale |
| 4,683,476 A | 7/1987 | Ferrari et al. |
| 4,711,233 A | 12/1987 | Brown |
| 4,736,738 A | 4/1988 | Lipovsek et al. |
| 4,755,797 A | 7/1988 | Kanaya |
| 4,794,046 A | 12/1988 | Nagai |
| 4,834,757 A | 5/1989 | Brantigan |
| 4,863,476 A | 9/1989 | Shepperd |
| 4,888,024 A | 12/1989 | Powlan |
| 4,969,888 A | 11/1990 | Scholten et al. |
| 4,978,357 A | 12/1990 | Goymann et al. |
| 5,030,238 A | 7/1991 | Nieder et al. |
| 5,059,193 A | 10/1991 | Kuslich |
| 5,064,439 A | 11/1991 | Chang et al. |
| 5,108,404 A | 4/1992 | Scholten et al. |
| 5,122,130 A | 6/1992 | Keller |
| 5,171,278 A | 12/1992 | Pisharodi |
| 5,192,326 A | 3/1993 | Bao et al. |
| 5,192,327 A | 3/1993 | Brantigan |
| 5,197,971 A | 3/1993 | Bonutti |
| 5,298,254 A | 3/1994 | Prewett et al. |
| 5,314,477 A | 5/1994 | Marnay |
| 5,431,658 A | 7/1995 | Moskovich |
| 5,439,684 A | 8/1995 | Prewett et al. |
| 5,443,514 A | 8/1995 | Steffee |
| 5,476,880 A | 12/1995 | Cooke et al. |
| 5,505,732 A | 4/1996 | Michelson |
| 5,514,180 A | 5/1996 | Heggeness et al. |
| 5,522,899 A | 6/1996 | Michelson |
| 5,554,191 A | 9/1996 | Lahille et al. |
| 5,571,109 A | 11/1996 | Bertagnoli |
| 5,571,189 A | 11/1996 | Kuslich |
| 5,591,235 A | 1/1997 | Kuslich |
| 5,620,458 A | 4/1997 | Green et al. |
| 5,645,084 A | 7/1997 | McKay |
| 5,645,599 A | 7/1997 | Samani |
| 5,653,763 A | 8/1997 | Errico et al. |
| 5,658,335 A | 8/1997 | Allen |
| 5,665,122 A | 9/1997 | Kambin |
| 5,702,454 A | 12/1997 | Baumgartner |
| 5,733,545 A | 3/1998 | Hood, III |
| 5,755,797 A | 5/1998 | Baumgartner |
| 5,756,127 A | 5/1998 | Grisoni et al. |
| 5,769,897 A | 6/1998 | Harle |
| 5,827,289 A | 10/1998 | Reiley et al. |
| 5,836,948 A | 11/1998 | Zucherman et al. |
| 5,860,977 A | 1/1999 | Zucherman et al. |
| 5,888,226 A | 3/1999 | Rogozinski |
| 5,891,147 A | 4/1999 | Moskovitz et al. |
| 5,899,939 A | 5/1999 | Boyce et al. |
| 5,951,553 A | 9/1999 | Betz et al. |
| 5,972,015 A | 10/1999 | Scribner et al. |
| 5,980,522 A | 11/1999 | Koros et al. |
| 5,984,922 A | 11/1999 | McKay |
| 5,989,289 A | 11/1999 | Coates et al. |
| 6,025,538 A | 2/2000 | Yaccarino, III |
| 6,033,411 A | 3/2000 | Preissman |
| 6,045,579 A | 4/2000 | Hochshuler et al. |
| 6,048,346 A | 4/2000 | Reiley et al. |
| 6,066,154 A | 5/2000 | Reiley et al. |
| 6,074,390 A | 6/2000 | Zucherman et al. |
| 6,102,950 A | 8/2000 | Vaccaro |
| 6,106,557 A | 8/2000 | Robioneck et al. |
| 6,110,179 A | 8/2000 | Flivik et al. |
| 6,110,210 A | 8/2000 | Norton et al. |
| 6,159,211 A | 12/2000 | Boriani et al. |
| 6,159,215 A | 12/2000 | Urbahns et al. |
| 6,159,244 A | 12/2000 | Suddaby |
| 6,190,414 B1 | 2/2001 | Young et al. |

(56) References Cited

U.S. PATENT DOCUMENTS

| | | | |
|---|---|---|---|
| 6,193,757 | B1 | 2/2001 | Foley et al. |
| 6,200,347 | B1 | 3/2001 | Anderson et al. |
| 6,206,923 | B1 | 3/2001 | Boyd et al. |
| D439,980 | S | 4/2001 | Reiley et al. |
| 6,235,043 | B1 | 5/2001 | Reiley et al. |
| 6,241,734 | B1 | 6/2001 | Scribner et al. |
| 6,241,771 | B1 | 6/2001 | Gresser et al. |
| 6,248,110 | B1 | 6/2001 | Reiley et al. |
| 6,273,916 | B1 | 8/2001 | Murphy |
| 6,279,916 | B1 | 8/2001 | Stecher |
| 6,287,308 | B1 | 9/2001 | Betz et al. |
| 6,287,309 | B1 | 9/2001 | Baccelli et al. |
| 6,309,420 | B1 | 10/2001 | Preissman |
| 6,387,130 | B1 * | 5/2002 | Stone ............... A61F 2/4455 623/17.16 |
| 6,395,034 | B1 | 5/2002 | Suddaby |
| 6,402,750 | B1 | 6/2002 | Atkinson et al. |
| 6,419,705 | B1 | 7/2002 | Erickson |
| 6,425,920 | B1 | 7/2002 | Hamada |
| 6,432,107 | B1 | 8/2002 | Ferree |
| 6,436,142 | B1 | 8/2002 | Paes et al. |
| 6,478,800 | B1 | 11/2002 | Fraser et al. |
| 6,488,710 | B2 | 12/2002 | Besselink |
| 6,500,205 | B1 | 12/2002 | Michelson |
| 6,562,074 | B2 | 5/2003 | Gerbec et al. |
| 6,595,998 | B2 | 7/2003 | Johnson et al. |
| 6,620,196 | B1 | 9/2003 | Trieu |
| 6,648,917 | B2 | 11/2003 | Gerbec et al. |
| 6,656,178 | B1 | 12/2003 | Veldhuizen et al. |
| 6,726,691 | B2 | 4/2004 | Osorio et al. |
| 6,740,093 | B2 | 5/2004 | Hochschuler et al. |
| 6,837,904 | B2 | 1/2005 | Ralph et al. |
| 6,852,126 | B2 | 2/2005 | Ahlgren |
| 6,852,129 | B2 | 2/2005 | Gerbec et al. |
| 6,852,095 | B1 | 3/2005 | Ray |
| 6,863,673 | B2 | 3/2005 | Gerbec et al. |
| 6,997,929 | B2 | 2/2006 | Manzi et al. |
| 7,118,580 | B1 | 10/2006 | Beyersdorff et al. |
| 7,799,034 | B2 | 9/2010 | Johnson et al. |
| 8,123,755 | B2 | 2/2012 | Johnson et al. |
| 8,974,464 | B2 * | 3/2015 | Johnson ............... A61B 17/025 606/90 |
| 9,655,743 | B2 * | 5/2017 | Johnson ............... A61F 2/4455 |
| 2002/0026195 | A1 | 2/2002 | Layne et al. |
| 2002/0147497 | A1 | 10/2002 | Belef et al. |
| 2002/0177897 | A1 | 11/2002 | Michelson |
| 2002/0183746 | A1 | 12/2002 | Zucherman et al. |
| 2003/0171812 | A1 | 9/2003 | Grunberg et al. |
| 2004/0019354 | A1 | 1/2004 | Johnson et al. |
| 2004/0064144 | A1 | 4/2004 | Johnson et al. |
| 2004/0220580 | A1 | 11/2004 | Johnson et al. |
| 2005/0149194 | A1 | 7/2005 | Ahlgren |

FOREIGN PATENT DOCUMENTS

| | | |
|---|---|---|
| FR | 2719763 | 11/1995 |
| WO | 9856301 | 12/1998 |
| WO | 9902214 | 1/1999 |
| WO | 9921500 | 5/1999 |
| WO | 0001527 | 2/2000 |
| WO | 0009024 | 2/2000 |
| WO | 0040177 | 7/2000 |
| WO | 0044319 | 8/2000 |
| WO | 0074608 | 12/2000 |
| WO | 0101895 | 11/2001 |

OTHER PUBLICATIONS

Cotton, Anne, MD et al.; Percutaneous Vertebroplasty: State of the Art; RadioGraphics; vol. 18, No. 2; pp. 311-323; Mar.-Apr. 1998.

Deramod, Herve, MD et al; Percutaneous Vertebroplasty with Polymethylmethacrylate; Interventional Procedures in Musculoskeletal Radiology I, Radiologic Clinics of North America; vol. 36, No. 3; pp. 533-546; May 1998.

European Search Report dated Sep. 9, 2009 related to corresponding European patent application No. 09007235.6.

Martin, J. B. et al.; Vertebroplasty: Clinical Experience and Follow-up Results Bone; vol. 1, No. 2, Supplement, pp. 11S-15S, Aug. 1999.

Rich, Kenneth J., MD et al.; Letters to the Editor; SPINE; vol. 25, No. 22; pp. 2968-2969; 2000.

Baddeley, S., et al; "The Use of Methylmethacrylate in the Treatment of Giant Tumors of the Proximal Tibia", Aust. N.Z. J. Surg., vol. 49, No. 1, Feb. 1979, (3 pp.).

Campanacci, M., et al.; "The Treatment of Tibial Plateau Fractures", Chi. Org. Mov. 72(3), Dec. 1975, Italian text (pp. 234-256) English translation.

Kyphon Surgical Technique Manual, 1999 (pp. 5, 6, 9, 16-19).

Kyphon web page, www.kyphon.com, Mar. 13, 2001, (1 p.).

Signus Medical, "TETRIS", Sep. 2003, (1 p.).

Blackstone Medical, Inc., "CONSTRUX™ PEEK VBR System", 2005, (1 p.).

* cited by examiner

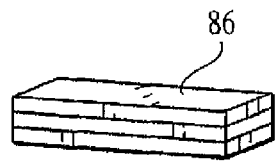
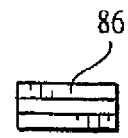
FIG. 6  FIG. 7
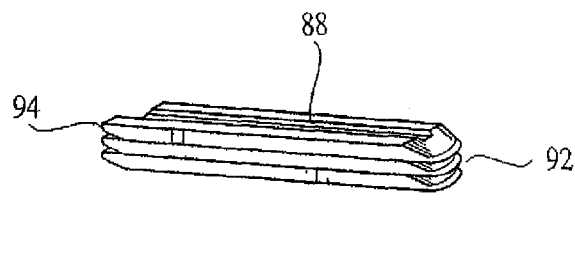
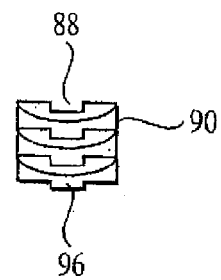
FIG. 8  FIG. 9
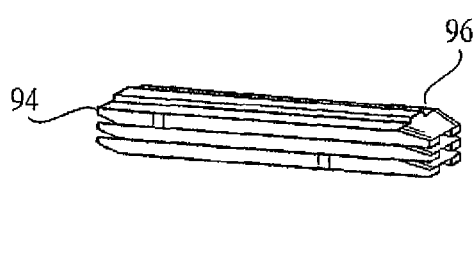
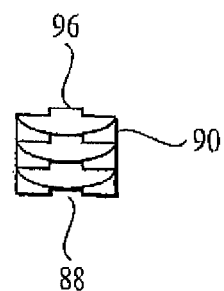
FIG. 10  FIG. 11

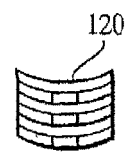
FIG. 18    FIG. 19
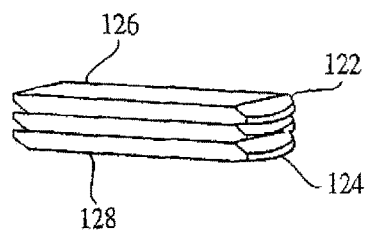
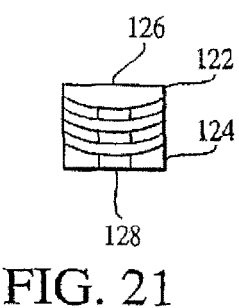
FIG. 20    FIG. 21
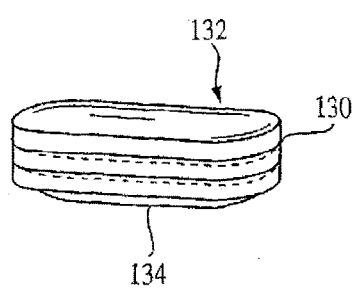
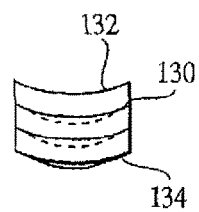
FIG. 22    FIG. 23
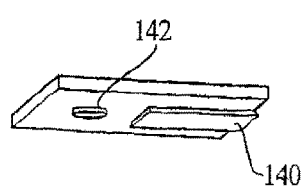
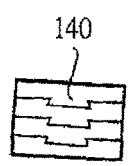
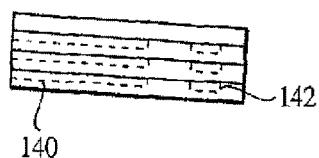
FIG. 24    FIG. 25    FIG. 26

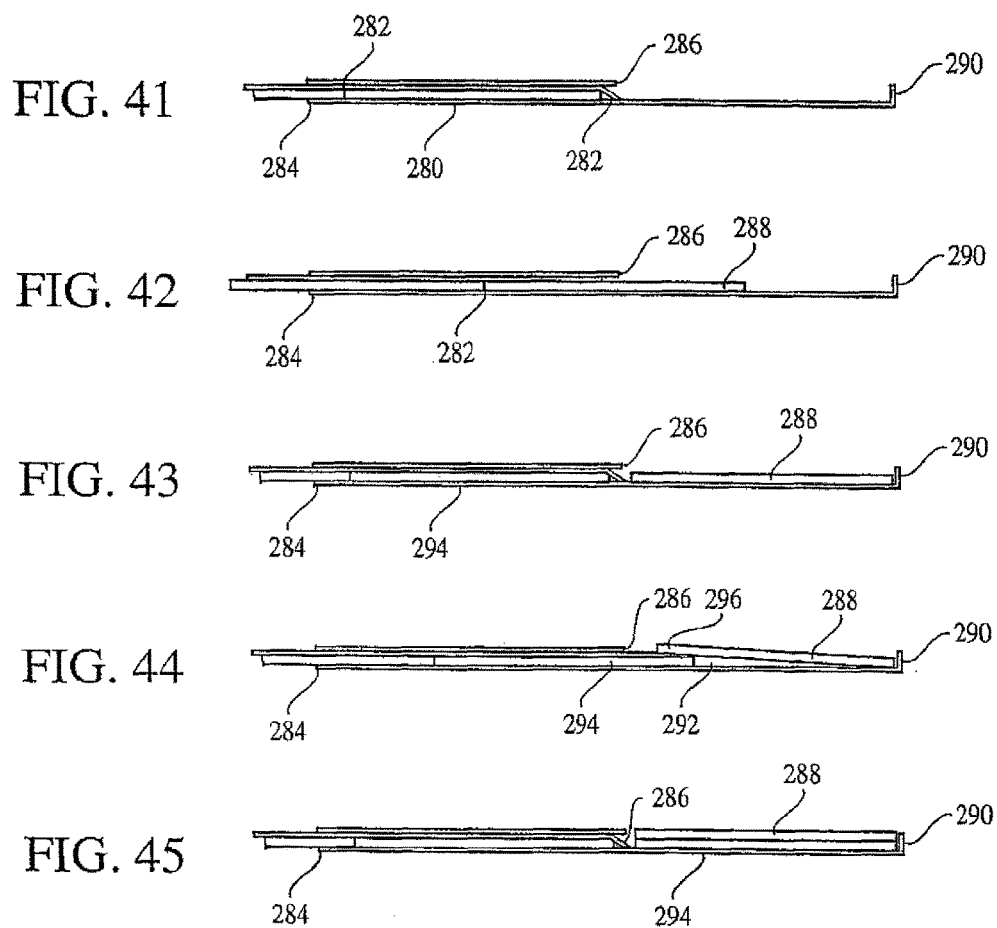

EXPANDABLE INTERBODY FUSION DEVICE

CROSS-REFERENCES TO RELATED APPLICATIONS

This application is a continuation of U.S. application Ser. No. 14/628,707, filed on Feb. 23, 2015, now U.S. Pat. No. 9,655,743, which is a continuation of U.S. application Ser. No. 14/027,421, filed on Sep. 16, 2013, now U.S. Pat. No. 8,974,464, which is a continuation of U.S. application Ser. No. 13/176,830, filed on Jul. 6, 2011, now U.S. Pat. No. 8,535,353, which is a continuation of U.S. application Ser. No. 11/867,746, filed on Oct. 5, 2007, now U.S. Pat. No. 8,123,755, which is a divisional of U.S. application Ser. No. 10/623,957, filed on Jul. 21, 2003, now U.S. Pat. No. 7,311,713, which is a continuation of U.S. application Ser. No. 09/872,905, filed on Jun. 1, 2001, now U.S. Pat. No. 6,595,998, which claims the benefit of priority to U.S. Provisional Application No. 60/274,372, filed on Mar. 8, 2001, the disclosures of which are incorporated by reference herein.

FIELD OF THE INVENTION

The present invention involves the field of surgery, and particularly surgical instruments and methods of using the same.

BACKGROUND OF THE INVENTION

A variety of physical conditions involve two tissue surfaces that, for treatment of the condition, need to be distracted from one another and then supported away from one another. Such distraction may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof. An optimal treatment method includes distracting and supporting the tissue surfaces simultaneously.

A minimally invasive distraction and support device would have significant application in orthopedic surgical procedures, including acute and elective procedures to treat bone fractures and degenerative changes of the skeletal system and including vertebral compression fractures, interbody fusion, vertebral disc augmentation or replacement, and other compression fractures including, but not limited to tibial plateau compression fractures, calcaneous compression fractures, distal tibia fractures, distal radius (wrist) fractures, crushed or fractured orbit and orthopedic oncology. Further, a minimally invasive distraction and support device would have application in non-orthopedic surgical procedures in plastic surgery (for example facial reconstruction), gastrointestinal surgery and urological surgery (for example the treatment of incontinence).

Vertebral Compression Fractures

A vertebral compression fracture is a crushing injury to one or more vertebrae. Vertebral fractures are generally associated with osteoporosis (the "brittle bone" disease), metastasis, and/or trauma. Osteoporosis reduces bone density, thereby weakening bones and predisposing them to fracture.

The osteoporosis-weakened bones can collapse during normal activity. In severe cases of osteoporosis, actions as simple as bending forward can be enough to cause a vertebral compression fracture. Vertebral compression fractures are the most common type of osteoporotic fractures according to the National Institute of Health. The mechanism of these fractures is one of flexion with axial compression where even minor events cause damage to the weak bone. While the fractures may heal without intervention, the crushed bone may fail to heal adequately. Moreover, if the bones are allowed to heal on their own, the spine will be deformed to the extent the vertebrae were compressed by the fracture. Spinal deformity may lead to breathing and gastrointestinal complications, and adverse loading of adjacent vertebrae.

Vertebral fractures happen most frequently at the thoracolumbar junction, with a relatively normal distribution of fractures around this point. Vertebral fractures can permanently alter the shape and strength of the spine. Commonly, they cause loss of height and a humped back. This disorder (called kyphosis or "dowager's hump") is an exaggeration of the spinal curve that causes the shoulders to slump forward and the top of the back to look enlarged and humped. In severe cases, the body's center of mass is moved further away from the spine resulting in increased bending moment on the spine and increased loading of individual vertebrae.

Another contributing factor to vertebral fractures is metastatic disease. When cancer cells spread to the spine, the cancer may cause destruction of part of the vertebra, weakening and predisposing the bone to fracture.

Osteoporosis and metastatic disease are common root causes leading to vertebral fractures, but trauma to healthy vertebrae also causes minor to severe fractures. Such trauma may result from a fall, a forceful jump, a car accident, or any event that stresses the spine past its breaking point. The resulting fractures typically are compression fractures or burst fractures.

Vertebral fractures can occur without pain. However, they often cause a severe "band-like" pain that radiates from the spine around both sides of the body. It is commonly believed that the source of acute pain in compression fractures is the result of instability at the fracture site, allowing motion that irritates nerves in and around the vertebrae.

Until recently, treatment of vertebral compression fractures has consisted of conservative measures including rest, analgesics, dietary, and medical regimens to restore bone density or prevent further bone loss, avoidance of injury, and bracing. Unfortunately, the typical patient is an elderly person who generally does not tolerate extended bed rest well. As a result, minimally invasive surgical methods for treating vertebral compression fractures have recently been introduced and are gaining popularity.

One technique used to treat vertebral compression fractures is injection of bone filler into the fractured vertebral body. This procedure is commonly referred to as percutaneous vertebroplasty. Vertebroplasty involves injecting bone filler (for example, bone cement) into the collapsed vertebra to stabilize and strengthen the crushed bone.

In vertebroplasty, physicians typically use one of two surgical approaches to access thoracic and lumbar vertebral bodies: transpedicular or extrapedicular. The transpedicular approach involves the placement of a needle or wire through the pedicle into the vertebral body, and the physician may choose to use either a unilateral access or bilateral transpedicular approach. The second approach, the extra-pedicular technique, involves an entry point through the posterolateral corner of the vertebral body. The needle entry point is typically 8 cm to 12 cm lateral of the mid-sagittal plane, with the skin incision typically closer to 8 cm in the proximal spine and generally closer to 12 cm in the distal spine. In general, one cannula is placed to fill the vertebral body with the extra-pedicular approach.

Regardless of the surgical approach, the physician generally places a small diameter guide wire or needle along the path intended for the bone filler delivery needle. The guide wire is advanced into the vertebral body under fluoroscopic guidance to the delivery point within the vertebrae. The access channel into the vertebra may be enlarged to accommodate the delivery tube. In some cases, the delivery tube is placed directly and forms its own opening. In other cases, an access cannula is placed over the guide wire and advanced into the vertebral body. After placement, the cannula is replaced with the delivery tube, which is passed over the guide pin. In both cases, a hollow needle or similar tube is placed into the vertebral body and used to deliver the bone filler into the vertebra.

In this procedure, lower viscosities and higher pressures tend to disperse the bone filler throughout the vertebral body. However, such conditions dramatically increase the risk of bone filler extravasation from the vertebral body. The transpedicular approach requires use of a relatively small needle (generally 11 gauge or smaller). In contrast, the extrapedicular approach provides sufficient room to accommodate a larger needle (up to 6 mm internal diameter in the lumbar region and lower thoracic regions). In general, the small diameter needle required for a transpedicular approach necessitates injecting the bone filler in a more liquid (less viscous) state. Further, the pressure required to flow bone filler through a small gauge needle is relatively high. The difficulty of controlling or stopping bone filler flow into injury sensitive areas increases as the required pressure increases. The larger needle used in the extrapedicular approach allows injection of bone filler in a thicker, more controllable viscous state. Therefore, many physicians now advocate the extrapedicular approach so that the bone filler may be delivered through a larger cannula under lower pressure.

Caution must be taken to prevent extravasation, with the greatest attention given to preventing posterior extravasation because it may cause spinal cord trauma. Physicians typically use fluoroscopic imaging to monitor bone filler propagation and to avoid flow into areas of critical concern. If a foraminal leak results, the patient may require surgical decompression and/or suffer paralysis.

Kyphoplasty is a modified vertebral fracture treatment that uses one or two balloons, similar to angioplasty balloons, to attempt to reduce the fracture and restore vertebral height prior to injecting the bone filler. Two balloons are typically introduced into the vertebra via bilateral transpedicular cannulae. The balloons are inflated to reduce the fracture. After the balloon(s) is deflated and removed, leaving a relatively empty cavity, bone cement is injected into the vertebra. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

Tibial Plateau Compression Fractures

A tibial plateau fracture is a crushing injury to one or both of the tibial condyles resulting in a depression in the articular surface of the condyle. In conjunction with the compression fracture, there may be a splitting fracture of the tibial plateau. Appropriate treatment for compression fractures depends on the severity of the fracture. Minimally displaced compression fractures may be stabilized in a cast or brace without surgical intervention. More severely displaced compression with or without displacement fractures are treated via open reduction and internal fixation.

Typically, the underside of the compression fracture is accessed either through a window cut (a relatively small resection) into the side of the tibia or by opening or displacing a splitting fracture. A bone elevator is then used to reduce the fracture and align the articular surface of the tibial condyle. A fluoroscope or arthroscope may be used to visualize and confirm the reduction. Bone filler is placed into the cavity under the reduced compression fracture to maintain the reduction. If a window was cut into the side of the tibia, the window is packed with graft material and may be secured with a bone plate. If a splitting fracture was opened to gain access, then the fracture is reduced and may be stabilized with bone screws, bone plate and screws, or a buttress plate and screws. (Both of these methods are very invasive and require extensive rehabilitation.)

Spinal Interbody Fusion

Spinal fusion is most frequently indicated to treat chronic back pain associated with instability or degenerative disc disease that has not responded to less invasive treatments. Fusion is also prescribed to treat trauma and congenital deformities. Spinal fusion involves removal of the spinal disc and fusing or joining the two adjacent vertebrae. The primary objective for patients suffering from instability is to diminish the patient's pain by reducing spinal motion.

Spinal fusions are generally categorized into two large groups: instrumented and non-instrumented. In non-instrumented procedures, the physician removes tissue from the unstable disc space and fills it with some form of bone graft that facilitates the fusion of the two adjacent vertebral bodies. Instrumented procedures are similar to non-instrumented procedures, except that implants (generally metallic) are also applied to further stabilize the vertebrae and improve the likelihood of fusion.

Conventional instrumented procedures generally utilize plates, rods, hooks, and/or pedicle screws through various surgical approaches. These conventional implants are secured to the vertebral bodies that are being fused. Interbody fusion devices were introduced in the 1990's as a less invasive surgical alternative, although interbody devices are increasingly being used in conjunction with pedicle screws. Interbody devices are implanted into the disc space to restore the normal disc spacing, utilizing tension in the annulus to stabilize the fusion unit. Interbody fusion provides a large area of the vertebral end plate for establishing bony fusion, a viable blood supply from the decorticated end plates, and dynamic compressive loading of the graft site. The interbody devices are generally filled with a bone filler to facilitate fusion. Interbody devices can be categorized in three primary groups: spinal fusion cages, which are available in a variety of shapes including rectangular, round-faced, and lordotic; allograft bone dowels and wedges (which are also available in various shapes); and titanium mesh (although titanium mesh is not itself a structural spacer).

Interbody fusion is typically completed through a posterior, an anterior, or a lateral intertransverse approach. Each of these techniques has limitations. Lumbar interbody fusion presents a challenging surgical procedure and relatively high pseudoarthrosis rates. As a result, this approach is increasingly combined with additional internal fixation devices such as pedicle screw fixation.

In all interbody surgical approaches, a relatively large opening is made in the annulus. The nuclear material is removed and the end plates are decorticated to facilitate bony fusion. Overall, the use of interbody devices has resulted in mixed clinical outcomes. Placement of a fixed height device presents challenges in proper tensioning of the annulus. For these and other reasons, there is concern over long-term stability of interbody devices and fusion mass.

SUMMARY OF THE INVENTION

The invention provides a combination of a temporary or long term implantable device and instrumentation to place the device, in which tissue surfaces are distracted along an axis to enable access to the space between the tissues. Generally, the invention provides wafers for stacking upon one another to provide an axially extending column to distract and support tissue surfaces. While a primary use of the invention is to reduce and stabilize vertebral compression fractures, the invention may be used in any situation where it is desirable to distract two tissue surfaces. The tissue may be bone, skin, soft tissue, or combinations thereof. Further, the surfaces may be opposed surfaces of contiguous elements or surfaces of opposed elements. Thus, the invention may be used to treat vertebral compression fractures, for replacement of vertebral discs, as an interbody fusion device, wedge opening high tibial osteotomy, tibial tuberosity elevation, as well as for treating other compression fractures including, but not limited to tibia plateau fractures, calcaneous, distal tibial fractures, or distal radius (wrist) fractures. The invention may also be used for restoring the floor of the orbit, for elevating soft tissue in cosmetic applications, or in incontinence applications as a urethral restrictor. Alternately, the invention may be used in similar veterinary applications.

The Distraction Device

The terms "vertical", "up", etc., are occasionally used herein for ease of understanding, and these terms should be taken in reference to the vertebrae of a standing patient. Thus, "vertical" refers generally to the axis of the spine. We may also utilize mutually perpendicular "X", "Y" and "Z" axes to describe configurations and movement, with the Z-axis being the axis of the column of wafers, that is, the direction in which this column grows as wafers are added sequentially to it. The X-axis refers to the axis extending generally in the direction of movement of each wafer as it is advanced to a position beneath a preceding wafer, and the Y-axis is perpendicular to both the X- and Z-axes. The wafers are sometimes described with reference to permitted degrees of freedom or restraint when they are placed in a column. It should be understood that these permitted degrees of freedom or restraint refer to the permitted or restrained movement of one wafer with respect to an adjacent wafer along one or more of the three axes, and the permitted or restrained rotation between adjacent wafers about one or more of these axes.

The distraction device includes a plurality of stackable wafers designed for insertion between tissue surfaces to form a column. The wafer column is assembled in vivo to provide a distraction force as well as support and stabilization of the distracted tissue. Preferably, the wafers place distraction force in one direction only and thus provide directional distraction. The distraction device may be permanently implanted, in which case the wafer column may be used alone or in conjunction with a bone filler material. Alternately, the distraction device may be used temporarily to manipulate tissues and then removed.

In use, the wafers are preferably stacked between two tissue surfaces as they are implanted, thereby distracting and supporting the tissue surfaces simultaneously. In the vertebral compression fracture application, it is preferable to distract along the Z-axis (along the axis of the spine) to restore vertebral height. However, in other applications, it may be preferable to provide distraction in a different direction. The features of a wafer and a column of wafers will be described relative to position and direction. The top of a wafer or the top of the column is defined as the face of the wafer or column in the direction of distraction. The bottom of a wafer or the bottom of the column is defined as the face opposite the top face. In similar fashion, above and below a wafer or column implies along the top and bottom of the wafer or column, respectively. Each wafer has a leading edge that enters the forming column first and a trailing edge opposite the leading edge. The sides of the wafer are adjacent the leading and trailing edges and the top and bottom faces of the wafer. In general, the sides are longer than the leading and trailing edges, however the sides may be shorter than the leading and trailing edges. The axis of the column is defined as a line parallel to the direction of distraction.

During implantation, the wafers are stacked to form a column to simultaneously distract and support the two tissue surfaces. The invention provides that trailing wafers can be positioned above or below the leading wafers to form a column. In one embodiment, the wafers are designed to be beveled at both their leading and trailing edges so that when lined up end-to-end, force on the trailing edge of the trailing wafer causes its leading edge to slide below the trailing edge of the leading wafer, thereby lifting up the leading wafer. Likewise, the bevel of the leading and trailing edges may be reversed enabling insertion of a trailing wafer above a leading wafer. Alternately, the leading and trailing edges may be chevron shaped or curved when viewed from the side, enabling insertion of trailing wafers between any two leading wafers or on the top or bottom of the column. In another embodiment, the wafers may be configured with blunt edges wherein the wafers are stacked with the insertion instrument. In all embodiments, by repeating the process with consecutive wafers, the column height increases to restore vertebral height.

The specific configuration of each wafer may be altered to better suit the application for which the wafer will be used. For instance, the thickness of the wafer and the angle of the bevel may be varied to provide a mechanical advantage and insertion force within acceptable ranges for a given application. A more acute bevel angle will provide greater vertical force for a given insertion force. In addition, wafer thickness may be varied to increase or decrease resolution available to the physician in performing a given surgical procedure. A thinner wafer will provide greater displacement resolution and incremental force generation to the physician in performing the procedure. A variation of wafer thicknesses may be used in combination to form a column and multiple wafers may be inserted into the column simultaneously. The top and bottom faces of a wafer may be parallel or oblique to enable building a column that is straight or curved, respectively. Parallel or oblique-faced wafers may be used independently or in combination to build a column that has straight and/or curved sections.

In order to place the wafers between the tissue surfaces, a wafer inserter is positioned within the surgical site with access at its distal tip to the tissue surfaces to be distracted and supported. A wafer is placed on the track and a plunger is used to advance the wafer to the distal end of the track.

This is repeated with consecutive wafers until a column of sufficient height is created per physician discretion. After the wafer(s) have been inserted, the insertion device is removed. The distal end of the insertion device may be manufactured from the same material as the wafers and/or be detachable. In this embodiment, the distal end of the insertion instrument would be detached after placing the wafer column, and the instrument removed.

Optionally, bone filler may be injected into the vertebra to further stabilize the distracted tissues. The first wafer inserted may be longer and/or wider than subsequent wafers. The size differential may facilitate bone filler flow around the wafers. In addition, the wafers can be designed with various tunnels, grooves, and/or holes to improve wafer encapsulation, bonding between the wafers and any injected bone filler, and to provide a pathway for bone filler to penetrate the wafer column.

BRIEF DESCRIPTION OF THE DRAWINGS

FIG. 6 shows a plan view of a configuration of distraction device according to one embodiment of the present invention.

FIG. 7 shows an alternate plan view of the distraction device configuration of FIG. 6.

FIG. 8 shows a plan view of a configuration of distraction device according to an alternate embodiment of the present invention.

FIG. 9 shows an alternate plan view of the distraction device configuration of FIG. 8.

FIG. 10 shows a plan view of a configuration of distraction device according to an alternate embodiment of the present invention.

FIG. 11 shows an alternate plan view of the distraction device configuration of FIG. 10.

FIG. 18 shows a plan view of a configuration of distraction device according to an alternate embodiment of the present invention.

FIG. 19 shows an alternate plan view of the distraction device configuration of FIG. 18.

FIG. 20 shows a plan view of a configuration of distraction device according to an alternate embodiment of the present invention.

FIG. 21 shows an alternate plan view of the distraction device configuration of FIG. 20.

FIG. 22 shows a plan view of a configuration of distraction device according to an alternate embodiment of the present invention.

FIG. 23 shows an alternate plan view of the distraction device configuration of FIG. 10.

FIG. 24 shows a plan view of a distraction device according to an alternate embodiment of the present invention.

FIG. 25 shows a plan view of a configuration of several of the distraction device of FIG. 24.

FIG. 26 shows an alternate plan view of the configuration of the distraction device of FIG. 25.

FIGS. 41-45 show sectional views of an embodiment of an insertion device according to the present invention, with corresponding suitable distraction device, in various states attendant to clinical deployment.

DETAILED DESCRIPTION OF THE PREFERRED EMBODIMENT

Figure 1:
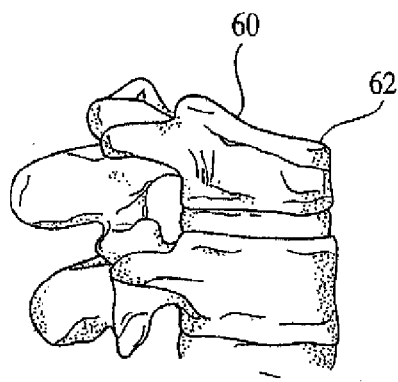
FIG. 1 shows a vertebral body having a compression fracture displacing its superior and anterior edge.
Figure 2:
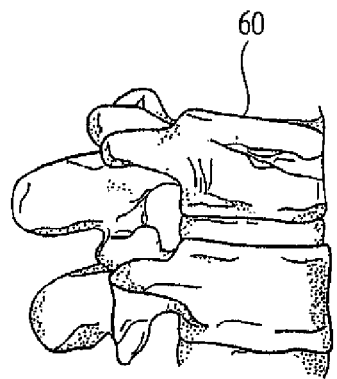
FIG. 2 shows a vertebral body, following treatment of a compression fracture.

The invention provides a combination of an implantable distraction device and instrumentation to place the device. The distraction device is detailed in this section by its application to the vertebral compression fracture. FIG. 1 shows a vertebral body 60 having a compression fracture displacing its superior and anterior edge 62. FIG. 2 shows a vertebral body 60 wherein the height has been restored.

The Distraction Device

A plurality of stackable wafers is provided for insertion between two tissues and is delivered to a surgical site along an axis transverse to the axis of distraction. Multiple wafer insertions result in a column of wafers at the surgical site that simultaneously distracts and supports the two tissues.

The wafers may be formed from a solid form of bone filler material, and/or any other suitable material such as but not limited to implantable grade alloys (including, but not limited to titanium, cobalt chrome, nitinol, or stainless steel), other medical grade composites (including, but not limited to polyetheretherketone polymer (PEEK), ultra-high molecular weight polyethylene, or polyethylene) other ceramics (including, but not limited to zirconia, alumina, or calcium-phosphate based ceramics), and resorbable polymers (for example, polylactic acid (PLA), polyglycolic acid (PGA), and poly(lactide-co-glycolide) (PLGA)). The wafers may be dense or porous, while porous wafers may be filled with resorbable polymers to increase mechanical strength. For soft tissue applications, it may be desirable to manufacture the wafers of woven collagen pads, tissue engineered materials, chitin, urethanes, silicone, or silicone materials. Alternately, the wafers may be manufactured from hydrogel (polyvinyl alcohol) in which the wafer is inserted in a dehydrated form and expands with fluids present at the insertion site. Hydrogel wafers may be particularly desirable for placing in the disc space between vertebrae. For purposes of this disclosure, these materials and their combinations will be collectively defined as the "implant materials." Further, the wafers and implant materials may be combined with osteoinductive agents (including BMPs, growth factors, cell therapy, gene therapy, and patient derived factors) and other drug therapies. The osteoinductive agents may be added to initiate and accelerate bone formation while the drug therapies may range from antibiotics to reduce the risk of infection to chemotherapy to treat cancer. Optionally, the wafers may be used with a flowable bone filler material. For the purposes of this disclosure, bone filler is defined as any substance used to stabilize the bone and includes, but is not limited to bone cement (polymethyl methacrylate PMMA, or PMA), other composite material, human bone graft (allograft or autograft), synthetic and xenograft derived bone substitutes (calcium phosphate, hydroxylapatite, and/or other ceramic based bone substitutes), collagen, or combinations of these materials.

Figure 3:
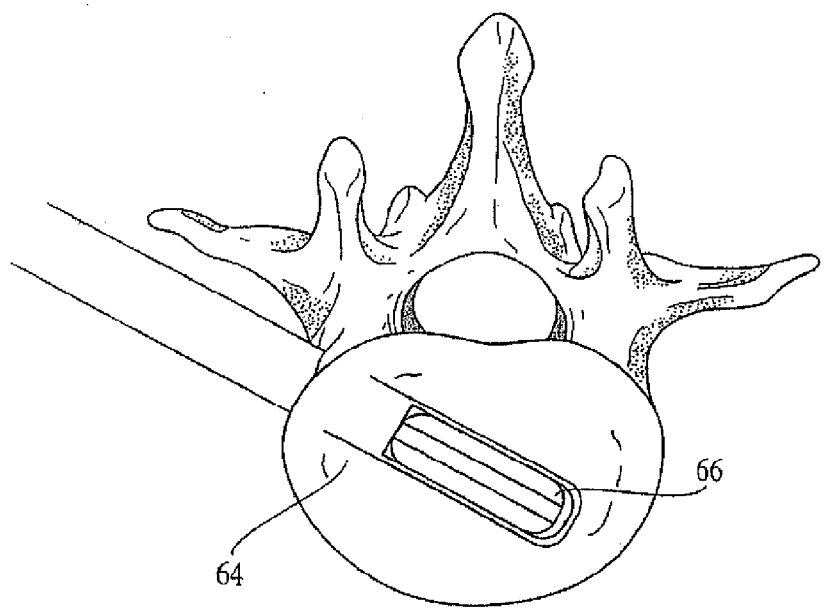
FIG. 3 illustrates a plan view of a distraction device insertion apparatus according to an embodiment of the invention, placed within a vertebral body shown in cross-section.

The invention provides that the wafer column is formed in vivo by using a wafer inserter. FIG. 3 illustrates a wafer inserter 64 placed within a vertebral body with a wafer 66 positioned distally on the wafer inserter 64. During implantation, the wafers are stacked to form a column to restore vertebral height. FIGS. 25 and 26 show a wafer column 192 supporting the proximal end plate of a vertebral body.

Figure 4:
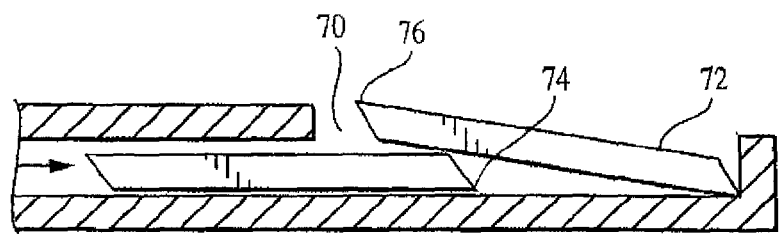
FIG. 4 illustrates a cross-sectional view of the insertion apparatus of FIG. 3 deploying a distraction device according to an embodiment of the present invention.

Consecutive wafer insertions result in a column of wafers at the surgical site. In one embodiment, the trailing edge of a wafer is beveled or otherwise configured to guide the next wafer under the first. FIG. 4 illustrates a wafer 70 being inserted under a preceding wafer 72. The leading edge 74 of the wafer is beveled to guide it under the one the trailing edge 76 of the preceding wafer, which is correspondingly beveled to guide the subsequent wafer underneath. Chevron and rounded edges may be used in the same manner as beveled edges to guide the leading edge of one wafer under the trailing edge of another. Alternately, the wafer edges may be squared and the tool for inserting the wafers may be used to lift the trailing end of the leading wafer and slide the trailing wafer thereunder as depicted in FIGS. 41-45. Similarly, any configuration of wafer or tool may be used to allow the wafers to stack into a column during insertion into the body.

The wafer design may be varied to suit the requirements of specific surgical applications. Wafer thickness may range from 0.2 mm to 6 mm, and bevel angle (the angle between the leading and trailing faces of a wafer and the direction of insertion) may range from 2 to 90 degrees. The mechanical advantage and the insertion force may be designed within acceptable ranges for a given application by varying the thickness and the bevel angle. A more acute bevel angle will provide greater vertical force for a given insertion force. In addition, wafer thickness may be varied to increase or decrease displacement resolution for a given surgical procedure. A thinner wafer will provide greater displacement resolution and incremental force generation.

Specifically for vertebral compression fracture applications, exemplary wafer dimensions range as follows:
Wafer length between 5 mm and 40 mm;
Wafer width between 2 mm and 16 mm;
Wafer thickness between 0.2 mm and 6 mm; and
Curved wafer radii between 10 mm and 500 mm.

These dimensions are provided only as guidelines and any suitable dimensions may be used. Furthermore, the dimensions of the wafer will likely vary widely when the wafers are used in other applications, such as, for example, treating tibial plateau fractures.

Figure 5:
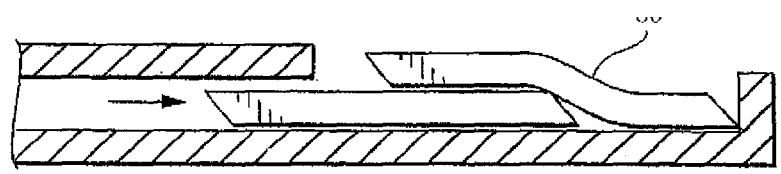
FIG. 5 illustrates a cross-sectional view of the insertion apparatus of FIG. 4 deploying a distraction device according to an alternate embodiment of the present invention.

The wafers may be rigid, as seen in FIG. 4, or may be flexible, as seen in FIG. 5. A rigid wafer may tend to pivot over the leading edge of the subsequent wafer as it is inserted, placing a bending moment on the wafer. A flexible wafer 80 tends to conform to the leading edge of the subsequent wafer as it is inserted. The stiffness of the wafer will be dependent on the material selected and the cross sectional geometry of the wafer. When stiffer materials are selected, the wafer thickness and bevel angle may be optimized to minimize the bending moment placed on the preceding wafer or wafers.

In addition, the wafer thickness may be uniform or varied. Specifically, the wafers may be either flat or wedged, or alternatively include a combination of flat and wedged wafers. The wedge may increase in thickness from leading edge to trailing edge or vice versa, or may increase in thickness from side to side. The wedged wafers may be of various angles. For example, the physician reducing a compression fracture may observe that the column is not parallel to the end plate. As the end plate is returning to its anatomical position, an appropriately wedged wafer(s) may be inserted to gradually curve the column to provide a parallel interface with the end plate. Similarly, the wafers may be wedge shaped with the anterior aspect of the wafer thicker than the posterior aspect to reproduce the natural lordotic curvature of the spine for interbody fusion. In addition, wafers of different thickness may be inserted into the same column.

A further option is to alter the interface of one wafer to a preceding or following wafer to suit a specific application. The interface may provide various degrees of freedom to accommodate various surgical applications. These include unconstrained, semi-constrained in select degrees of freedom, and totally constrained applications. Changing the wafer's surface configurations often varies the wafer interfaces. The surface configurations may be applied independently or in combination, based on the demands of the surgical application.

For example, if the wafers are to be implanted in a fashion that does not require alignment of one wafer to the next wafer, the interfaces between the wafers may be generally flat. This configuration provides a simple unconstrained wafer interface. The generally flat contact faces allow the wafers to translate relative to one another in the plane of the interface. They are also free to rotate about an axis normal to the interfaces. Optionally, the wafers may be distracted from one another.

An unconstrained wafer configuration is shown in FIG. 6 where the wafers 86 are flat wafers with no surface texture, that is, with surfaces that may rigidly slide on one another. These wafers are limited in compression along the Z-axis and rotation about the X- and Y-axes. However, distraction along the Z-axis is free. Translation and rotation are permitted along the X- and Y-axes in the plane of the interface. FIG. 7 provides an end view of the flat wafer 86 configuration.

On the other hand, if a semi-constrained wafer interface is desired, the wafers may be otherwise configured. For example, if the wafers are designed for placement in a vertical column wherein they are allowed to slide longitudinally, then the interfaces between the wafers may have a longitudinal groove 88 to align the wafers as shown in FIGS. 8 and 9. FIGS. 8-11 illustrate a preferred wafer embodiment. The wafers 90 have beveled leading edges 92 and beveled trailing edges 94 to facilitate sliding of a subsequently inserted wafer under the leading wafer. As seen in FIGS. 8 and 9, the wafers 92 include ridges 96 along their bottom surfaces and corresponding grooves 98 along their top surfaces to limit motion of one wafer to another. Similarly, the ridge may be located along the top wafer surface and the groove located on the bottom surface, as shown in FIGS. 10 and 11.

Figure 12:
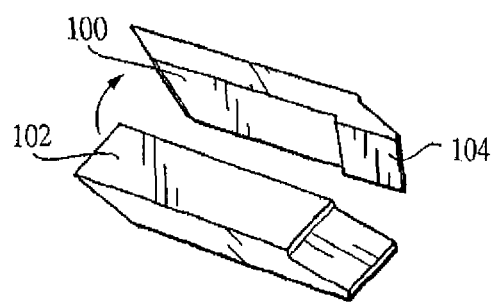
FIG. 12 shows a plan view of a configuration of distraction device according to an alternate embodiment of the present invention.
Figure 13:
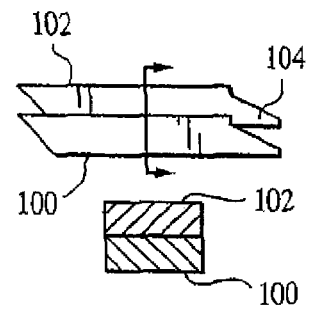
FIG. 13 shows a sectional view of the distraction device configuration of FIG. 12.
Figure 14:
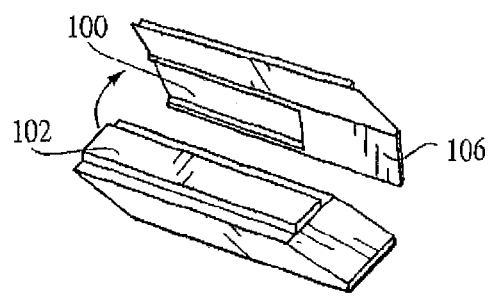
FIG. 14 shows a plan view of a configuration of distraction device according to an alternate embodiment of the present invention.
Figure 15:
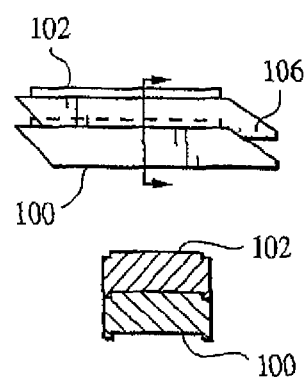
FIG. 15 shows a sectional view of the distraction device configuration of FIG. 14.
Figure 16:
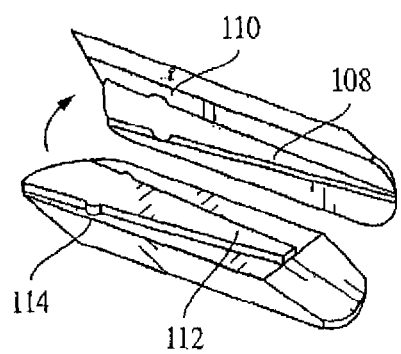
FIG. 16 shows a plan view of a configuration of distraction device according to an alternate embodiment of the present invention.
Figure 17:
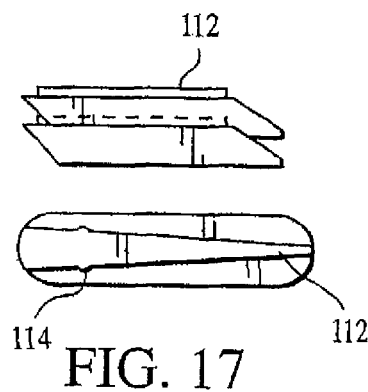
FIG. 17 shows an alternate plan view of the distraction device configuration of FIG. 16.

As shown in FIGS. 12-15, the wafer may have a "lip" built into the undersurface 100 and corresponding ridge 102 on the top surface of the subsequent wafer to limit axial travel of the subsequent wafer along the X-axis or Y-axis as desired. The undersurface 100 is the surface of the wafer adjacent to the insertion track. The lip 104 can extend along the leading edge of the wafer (preventing translation along the X-axis) as seen in FIGS. 12 and 13, or the lip can extend along the lateral (not leading or trailing) edges of the wafer (preventing translation along the Y-axis), or as shown in FIGS. 14 and 15, the lip 106 can extend along the lateral edges and the leading edge (preventing translation along the X- and Y-axes). However, the lip should not extend along the trailing edge of the wafer as such a configuration may interfere with the interface between the wafer and the subsequent wafer. Furthermore, FIGS. 16 and 17 illustrate the lip in a tapered configuration 108 with a mechanical detent 110 along the length of the taper. A corresponding tapered ridge 112 along top of the subsequent wafer engages the tapered lip 108. Similarly, the mechanical detents 114 on the tapered ridge 112 engage the corresponding mechanical detents 110 in the tapered lip 108. The tapered lip may be configured without mechanical detents wherein the taper angle would be such to promote a frictional lock between the wafers when axially loaded. Alternatively, the groove may be a dovetail to provide longitudinal sliding and a vertical lock between the wafers.

Another wafer embodiment, shown in FIGS. 18 and 19, involves wafers 120 having cylindrical (arched surface) interfaces. The axis of the cylinder is along the X-axis of the wafer, allowing adjacent wafers to slide along an arch about the X-axis. Such motion enables the top and the bottom of the column to conform to non-parallel tissue support surfaces while applying a distraction force to the tissue surfaces. The wafers are restricted in translation in the Y-axis and rotation about the Z-axis. If desired, the top 122 and bottom 124 wafers of a cylindrical column may have flat top 126 and bottom 128 surfaces respectively, as seen in FIGS. 20 and 21, to facilitate uniform support by tissue support structures.

FIGS. 22 and 23 show an alternate wafer design providing semi-constrained wafer interfaces 130. The wafers have spherical (or, optionally, hemi-spherical or less than hemi-spherical) interfaces that provide rotation about all three-principle axes. In this embodiment, translation along the X- and Y-axes and compression along the Z-axis are restricted. Distraction along the Z-axis and rotation about the Z-, Y-, and X-axes are free. Optionally, the top and bottom wafers may be flat (not shown) on their top 132 and bottom 134 surfaces respectively. If flat, the top 132 and bottom 134 surfaces facilitate uniform support from support structures.

In another embodiment, the semi-constrained wafer interfaces may be pinned to one another allowing rotation in the plane of the interface about a fixed axis.

In yet another embodiment of semi-constrained wafer interface, the wafer interfaces may be keyed together to prevent distraction of the wafers. Such keyed interfaces may include but are not limited to a dovetail (see for example FIG. 24), "T" bolt, or key hole design that allows the wafers to translate along the axis of the keyed elements. Translation normal to the keyed elements, distraction, and rotation are restricted.

Another option is to constrain the wafer interfaces. In one such embodiment, the wafer interface includes a combination of a keyed element and a snap-in pin that can be used to allow sliding one wafer onto another to provide lifting force. The keyed elements provide restriction of translation normal to the keyed element and distraction and rotation. The addition of a pinned element that snaps in place provides restriction of translation along the axis of the keyed element.

FIGS. 24-26 show a wafer configuration combining a dovetail 140 and a cylindrical indent 142. This limits compression and distraction along the Z-axis, translation along the X- and Y-axes and rotation about the X-, Y-, and Z-axes. Thus, the wafers are constrained in all degrees of freedom.

Alternately, a constrained wafer interface may include a series (two or more) of pressfit pinned interlocks that engage when one wafer is properly positioned above another and the two wafers are compressed together.

If the wafers are intended for stacking in a vertical column with translation locked, the wafer interfaces may be keyed together with a boss on each wafer that fits into a mating cavity on an adjacent wafer. The boss may be of any suitable shape, such as cylindrical or square. Further, if vertical locking is needed, the boss feature may be combined with a dovetail or other keyed mechanism to lock the wafers from vertical separation.

Figure 46:
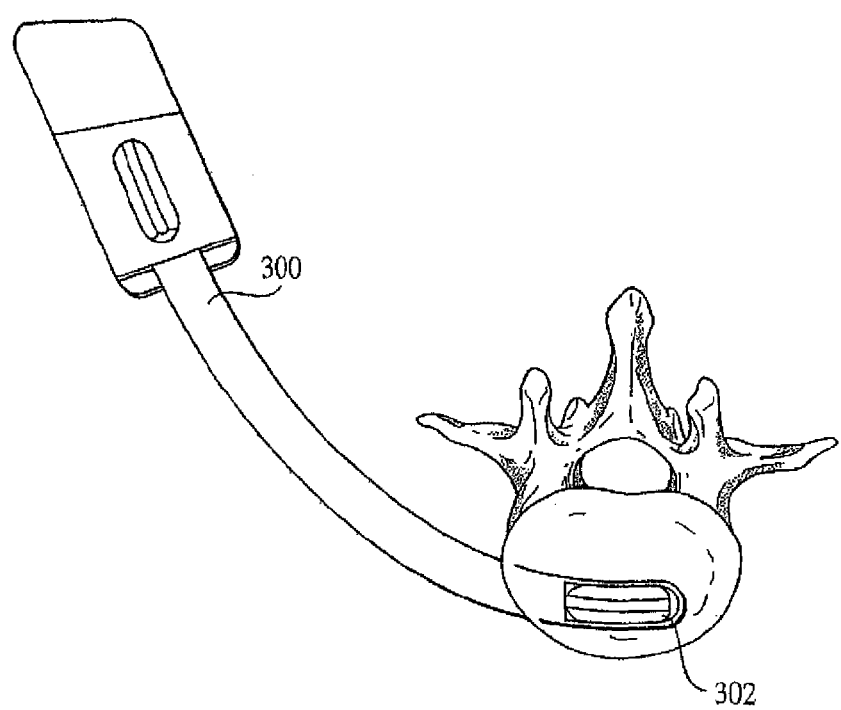
FIG. 46 shows a plan view of a clinical deployment device according to an alternate embodiment of the present invention, inserted into a vertebral body, shown in cross-section.

A further wafer option is to alter the shape of the wafers. The wafers may be straight or may be curved along a constant radius extending from an axis parallel to the axis of the desired wafer column. In the case of straight wafers, stacking is longitudinal and the insertion instrument deploys the wafers linearly. In the case of curved wafers, stacking is along the arch of the curve and the insertion instrument deploys the wafers along an arch. Reference is made to FIG. 46. Alternatively, the curved wafers may have a ridge on the top surface of slightly different configuration than that of the mating groove on the under surface thereby creating a frictional lock when one wafer is inserted under another. In all wafer embodiments containing mating ridges and grooves, the ridges are described as being on the top surface of the wafer and the groove on the bottom surface. The wafers would function equivalently if the groove were on the top surface and the ridge on the bottom surface.

In certain applications, it may be beneficial for the wafers to be secured to one another after insertion. Any suitable method for securing the wafers to one another as known by those skilled in the arts may be used. Wafers may be secured to one another by means of an adhesive bond, a chemical bond, and/or a mechanical interlock (as described above). Applying a generic fluent adhesive, for example cyanoacrylate, into the cavity surrounding the column provides adhesive bonding. The fluent adhesive hardens and locks the wafers.

Introducing a liquid material that is chemically equivalent to the wafer provides a potential chemical bonding. For example, the wafers may be manufactured from bone cement and bone cement may be injected around the wafers and into the vertebral body. The monomer in the bone cement may initiate a chemical bonding between the wafer and the bone filler, thereby locking the wafers together. A stable construct combined with cement interdigitation is believed to provide stability and pain relief in a crushed vertebra.

It is also possible to enhance the wafer-to-wafer bonding and the wafer-to-bone filler bonding should bonding be desired. One method for doing so involves solvent bonding in which the wafers are wiped with an appropriate solvent as they are inserted into the vertebra. A second method involves coating the wafers with a microencapsulated solvent. The setting or hardening time for adhesives or solvent bonding may be designed to allow time to properly position the wafer column. Alternatively, the adhesives or solvents may be activated by additional means such as light, heat, an activator, or other means that allow placing and positioning the wafers before securing them to one another.

A preferred method of wiping the wafers with solvent includes equipping the wafer inserter with a reservoir of solvent. A channel and wick design transports solvent to the distal end of the wafer inserter. As the wafers are inserted, they pass over the wick coating them with solvent. Once inside the vertebra and formed as a column, the wafers become bonded to each other by solvent bonding. The solvent may also enhance the bonding of the wafers to the bone filler that may be injected later in the procedure.

In order to coat the wafers with a layer of micro spheres containing solvent, the wafers are coated prior to insertion. As the wafers are passed through the wafer inserter and slide across one another in the column, the micro spheres are ruptured to release the solvent. The solvent then bonds the wafers to one another and preps the outer surface to enhance bonding to the bone filler injected later.

The wafers may also include tunnels, grooves, or holes to facilitate movement of bone filler through the wafer column into the surrounding bone. Further, openings may be provided through the wafers to allow communication between the tunnels, grooves, or holes or adjacent wafers. In any configuration, bone filler material injected into the wafer column would then flow through the column, fully encapsulating the wafers and better bonding the wafers to the bone filler.

A preferred wafer embodiment includes radiopacity to enable visualization. For example, a radiopaque material such as a metal marker or barium sulfate may be combined with the wafer material when the wafers are manufactured. Injection molding of the wafers with an x-ray marker inside the wafer, machining the wafers with a pressfit hole for an x-ray marker, applying a layer of radiopaque epoxy, or bonding a radiopaque marker onto the surface of the wafer are other non-limiting examples of inclusion of radiopaque materials. Alternatively, the first and last wafers may be made of a suitable radiopaque material, such as metallic or plastic, to enable visualization of the top and bottom of the forming wafer column under fluoroscopy.

Figure 27:
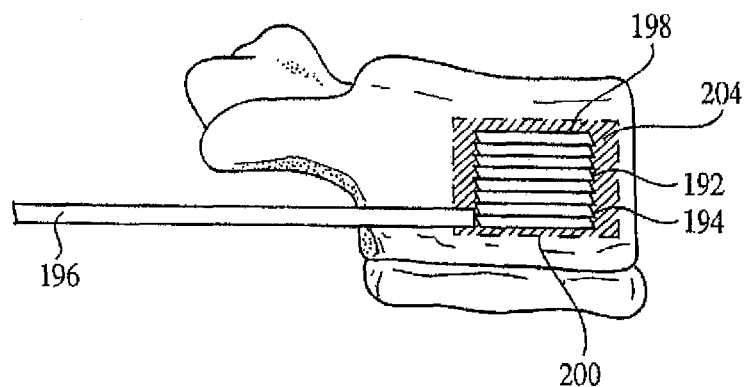
FIG. 27 shows a plan view of a configuration of distraction device deployed within a vertebral body, shown in sectional view.
Figure 28:
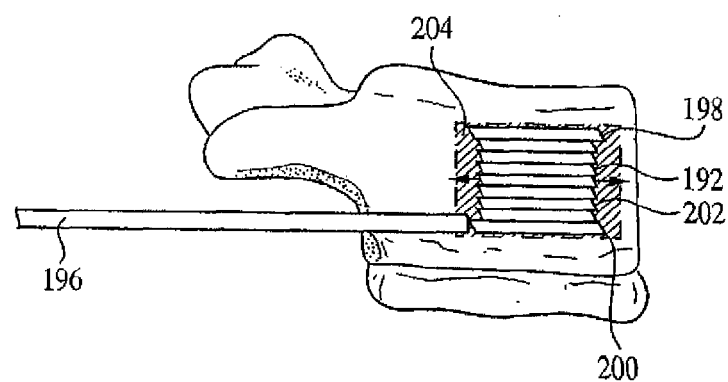
FIG. 28 shows a plan view of a further configuration of distraction device being deployed within a vertebral body, shown in sectional view.

In a clinical application, the wafers are inserted such that consecutive wafer insertions form a column. FIG. 27 illustrates a column 192 formed of equally sized wafers 194 inserted through wafer inserter track 196. However, in some situations it may be desirable to configure the top 198 and bottom 200 wafers of the column 192 larger than the intermediate wafers 202 as shown in FIG. 28. The larger top and bottom wafers will provide larger surface area over which to distribute loads. As the larger, first wafer is elevated, a space is created between the edges of the subsequent wafers and the surrounding tissue. This space would be equivalent to the overhang of the first wafer. The final wafer, or alternatively, the detachable distal end of the inserter, may also be larger than intermediate wafers 108 so as to create an overhang similar to that of the first wafer while also increasing the contact area. The end result is a channel around the interspaced wafers through which the bone filler may flow to fully encapsulate the wafers and to interdigitate with surrounding tissue 204.

Figure 29:
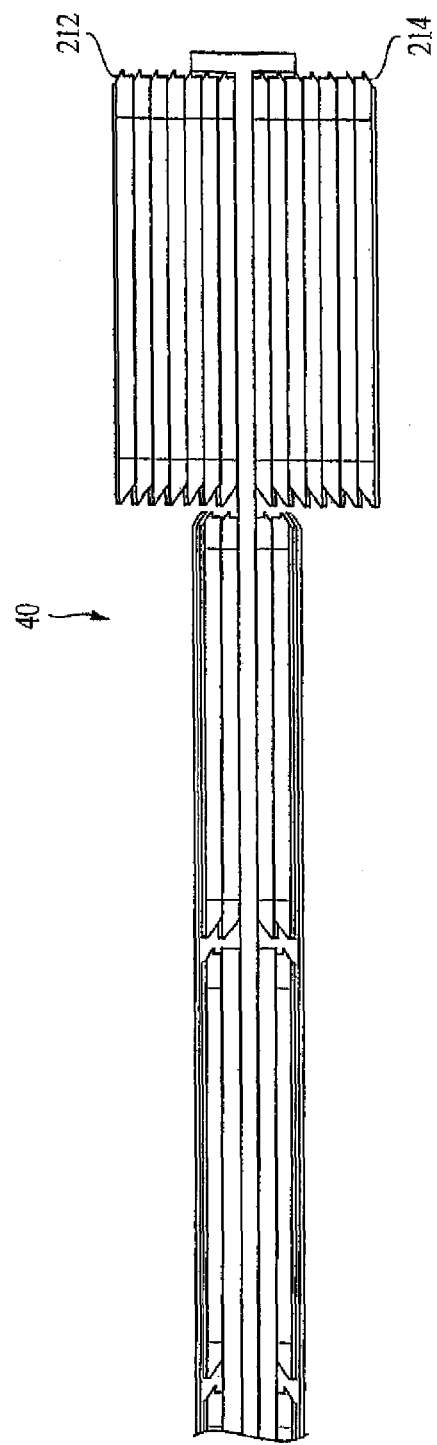
FIG. 29 show a sectional view of a portion of an insertion device according to one embodiment of the present invention.
Figure 30:
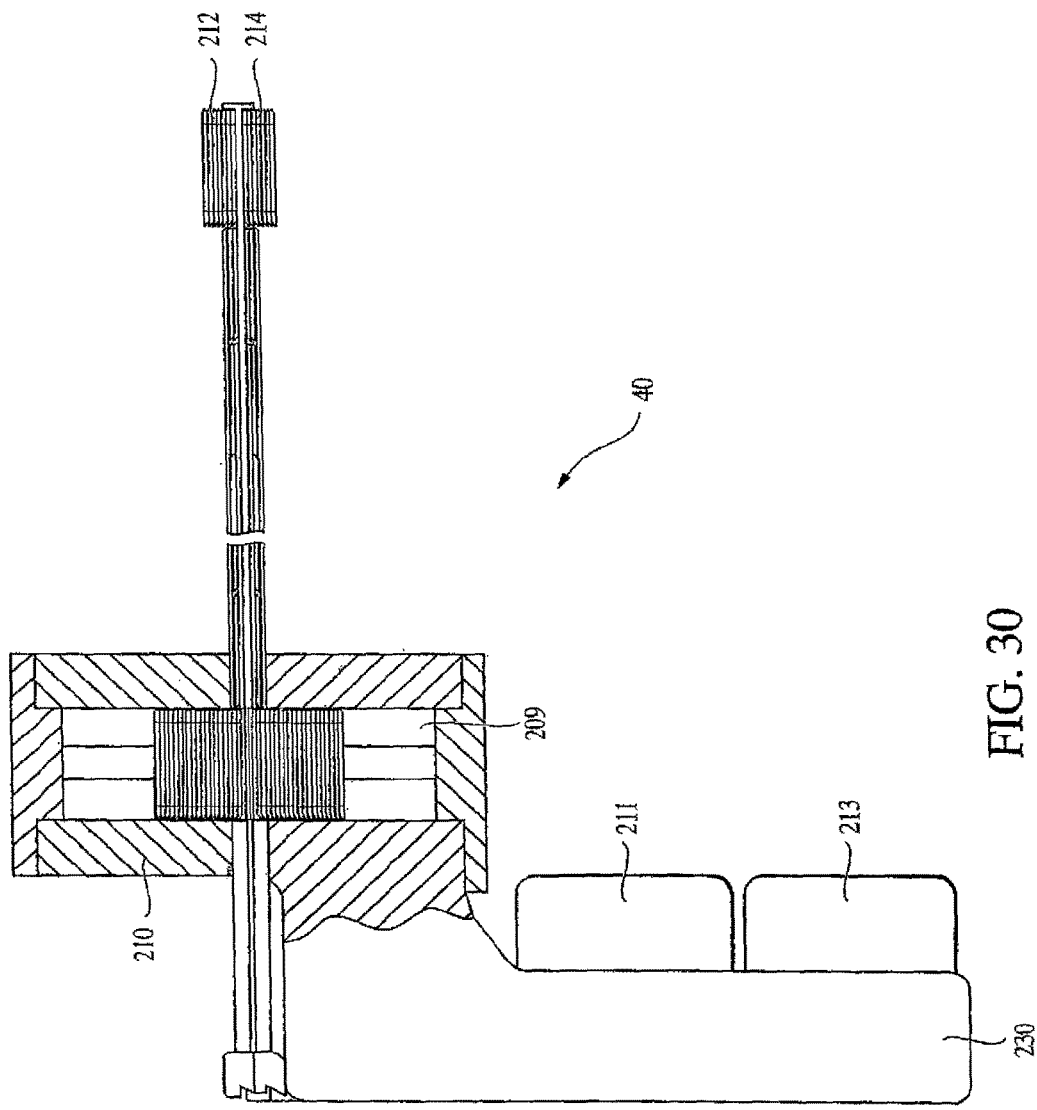
FIG. 30 shows a sectional view of an entire insertion device, a section of which is depicted in FIG. 29.

It may be advantageous to form multiple wafer columns extending axially in opposite directions. This can be done by a variety of different methods. One method involves using multiple wafer inserters. For example, if two opposing wafer columns are to be formed, then one wafer inserter is deployed to form a wafer column directed superiorly, while a second wafer inserter is deployed to form a wafer column inferiorly, opposite the first column. The separate wafer inserters may have different access locations through the cortical wall of the vertebral body. The wafer inserters may be parallel to one another, or skewed to one another, or one may enter the vertebral body through the ipsilateral cortex relative to the first wafer inserter. In addition, the wafer inserters may be adjacent one another or may be separated by cancellous bone. Alternately, as seen in FIGS. 29 and 30, a single wafer inserter 40 might be used wherein the wafer inserter is able to deploy wafers in opposing directions, one column deployed superiorly 212 and the other deployed inferiorly 214. Deployment of wafers in each direction may be independent, in which case the physician, based on intraoperative assessment, may expand the wafer column proximally or distally as needed. Alternatively, wafer deployment may be simultaneous in each direction, in which case a wafer would be added to the wafer columns forming in opposing directions.

Figure 31:
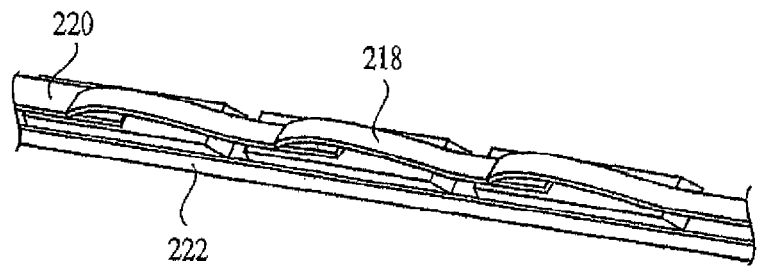
FIG. 31 show a plan view of a series of undeployed distraction devices connected by a tether according to one embodiment of the present invention.
Figure 32:
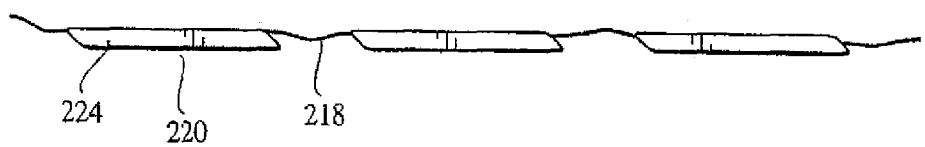
FIG. 32 shows a plan view of an alternate state of the distraction devices of FIG. 31.

The wafers may be connected, prior to implantation, by a tether. The tether may be a thin ribbon manufactured of nitinol, suture, ribbon, or similar material. The tether may be thin and rope-like or wide and band-like. FIG. 31 shows an embodiment where the tether 218 runs along the top surface (224 of FIG. 32) of the wafer 220. The wafers 220 are placed in the track 222 with the tether 218 connecting them. A side view of the same embodiment is shown in FIG. 32. Connection via the tether allows the wafers to be easily removed after placement. When a tether is used to connect the wafers, the wafers may also be formed with grooves or surface configurations to control translational movement.

Preferably, the wafers are molded around a tether wherein the tether is positioned at the top of the wafers to form a continuous sliding surface. The sliding surface prevents the wafers from "catching" on the wafer inserter as they are removed from the surgical site through the wafer inserter. The wafer is pulled up to the leading edge of the track and the tether provides a smooth transition as the wafer is fed into the track during extraction. The length of the tether is slightly longer than the length of a wafer to facilitate stacking the wafers in vivo.

Figure 33:
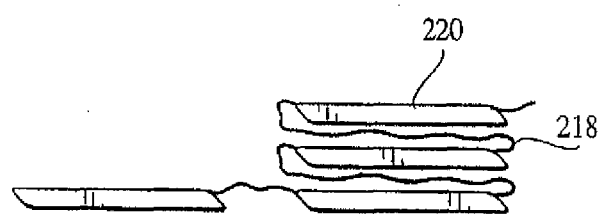
FIG. 33 shows a plan view of an alternate state of the distraction devices of FIG. 31.

The wafers connected via a tether are especially useful when the wafers are used as a bone tamp. This configuration may be used in situations where it is desirable to form a space between tissues and then remove the column. FIG. 33 shows an expanded column formed of wafers 220 connected via a tether 218 to illustrate the path of the tether as the column is formed. An implant manufactured from any of the materials previously described may be placed in the cavity created by the removed column of wafers, or bone filler may simply be injected.

Further embodiments of the connected wafer configuration include using two tethers running along the lateral edges of the top surface of the wafers. The wafers and tether may alternately be integrally formed as a continuous string of wafers. In this embodiment, the string of wafers is configured from a continuous piece of material wherein the wafers and tether are integrally formed. The tether enables stacking of the wafers. Yet another embodiment involves placing a wire mesh formed of small diameter wire, for example 0.001", along the top surface of the wafers. The wire is optionally stainless steel, nitinol, or other suitable metal or plastic or fabric. Furthermore, the wafers may be spaced and secured inside a woven tube to enable stacking of the wafers once inserted by the wafer inserter. The wire tube is woven of a wire mesh formed of a small diameter wire, for example 0.001" diameter. The tube has a circumference equal to the cross-sectional circumference of a wafer.

The Wafer Inserter

A wafer inserter is provided as part of the invention to deliver the wafers to the surgical site and to form a column of wafers. In one embodiment, the wafer inserter applies a force along the X-axis (the axis of insertion) to a wafer that is to be added to the column. As previously described, the wafers may be configured with beveled ends to facilitate lengthening along the Z-axis of the column as the additional wafer is inserted. In an alternate wafer embodiment also previously described, the edges of the wafers are squared and the wafer inserter raises the leading wafer to place the trailing wafer thereunder.

Numerous variations of the wafer inserter are possible, the embodiments generally including, but not limited to, a track, a plunger, and a cartridge. The wafer inserter is comprised of a track, which is a long narrow channel through which wafers pass when placed into the wafer column. A plunger generally advances wafers down the track. Multiple wafers are housed in a cartridge of the wafer inserter for advancement down the track. Preferably included is a mechanism for feeding subsequent wafers into the track in front of the plunger. Further, the track is configured for removal from the surgical site while leaving the wafer column intact.

In a hand-held embodiment, a mechanical mechanism is provided for converting grip strength into a force to advance the plunger. The wafer inserter may include a device to measure the force applied to the plunger or along the axis of the wafer column. This device may be, for example, a force transducer. A device, for example a counter, may also be included to monitor the number of wafers inserted. The total force applied may be thus monitored and may reference a preset adjustable force guideline. A device to display the measured force and/or the number of wafers inserted may also be included. It may be desirable to provide a mechanism to limit the force applied along the axis of the wafer column as well as means for the physician to adjust such force. Additionally, in order to inject bone filler to further stabilize the wafer column, a means to open the channel of the track to accommodate such bone filler may be provided.

Figure 34:
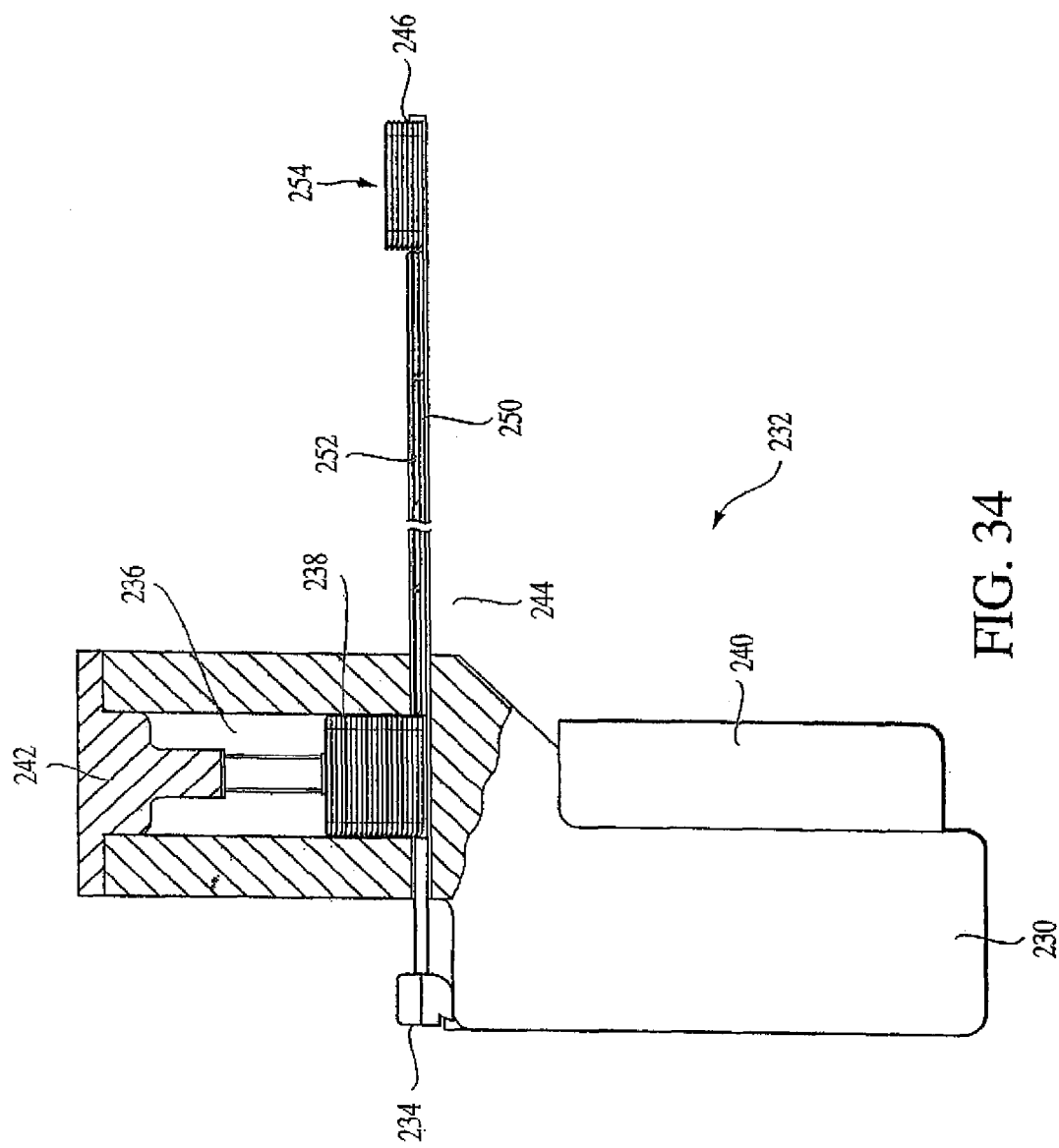
FIG. 34 shows a sectional view of an insertion device according to one embodiment of the present invention.
Figure 35:
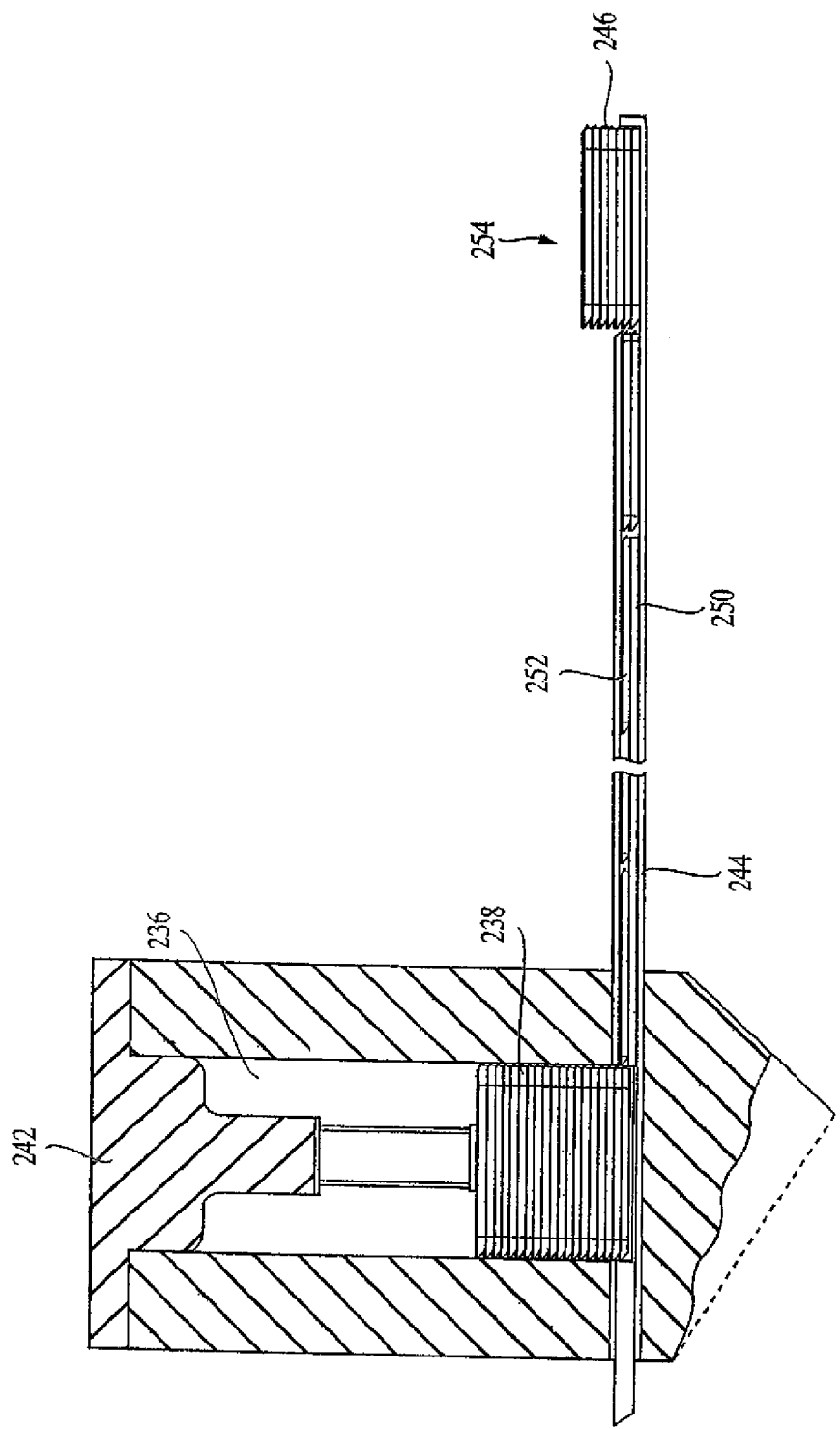
FIG. 35 shows a sectional view of a portion of the insertion device of FIG. 34.
Figure 36:
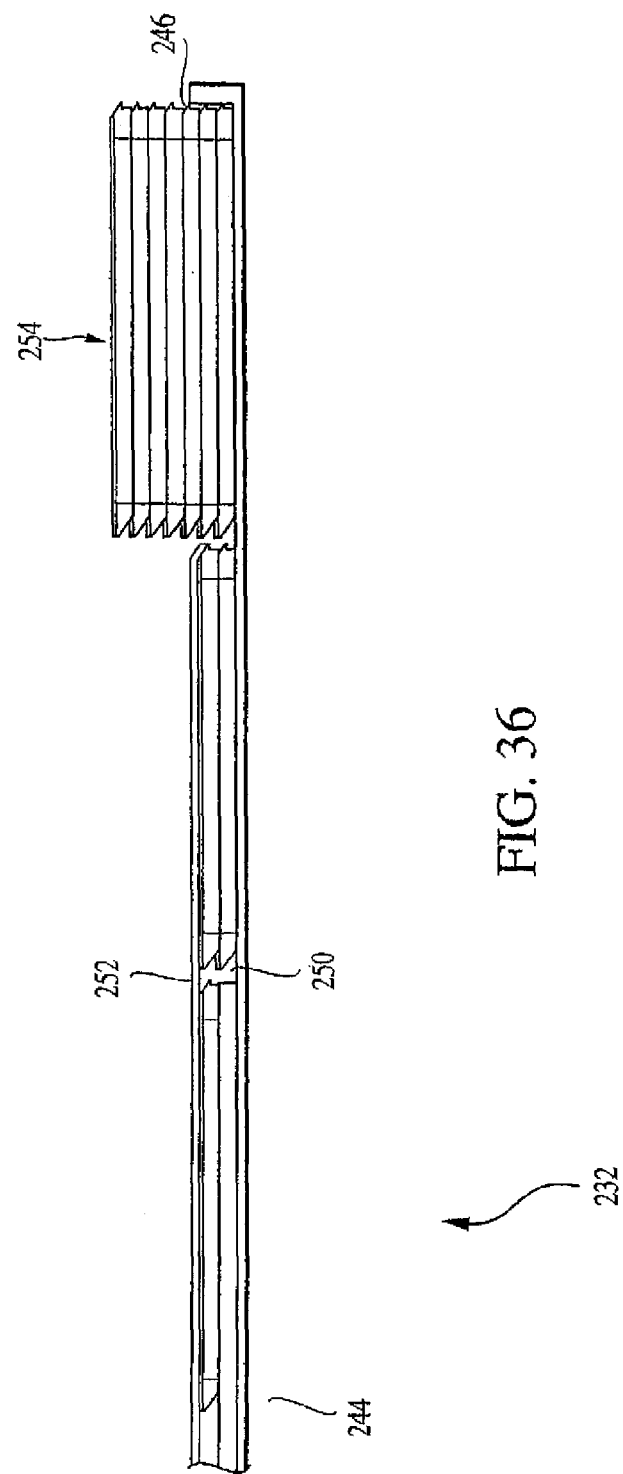
FIG. 36 shows a sectional view of a portion of the insertion device of FIG. 35.

One embodiment of the wafer inserter is illustrated in FIG. 34. The handle 230 may be gripped to position the wafer inserter 232. The wafer inserter 232 has, at its proximal end 234, a magazine 236 containing wafers 238. The wafers 238 may be stacked in the magazine 236 with a top surface of one wafer supporting the bottom surface of an adjacent wafer. The handle 230 is equipped with a trigger 240 for forcing wafers out of the magazine 236. Optionally, the magazine 236 is equipped with a spring 242 to load wafers 238 along the track 244 of the inserter 232. The track 244 of the inserter 232 extends from the magazine 236 to the surgical site at its distal end 246. As they enter the wafer track 244, the wafers 238 are aligned with the leading edge of one wafer adjacent the trailing edge of a preceding wafer. The track 244 in the embodiment shown in FIG. 34 includes a lower cavity 250 and an upper cavity 252. The plunger extends through the lower cavity 250 while the wafers 238 are aligned along the upper surface of the plunger. An opening is provided along the top surface of the lower cavity 250 at the distal end 246 of the track 244 to accommodate a wafer. Thus, as the plunger is retracted past the trailing edge of the furthest distal wafer, the wafer drops into the lower cavity. The plunger pushes the wafer distally to form a column of wafers 254. FIG. 35 provides a close up of the wafer inserter magazine 236, track 244, and distal end 246. FIG. 36 shows an extreme close up of the distal end 246 of the wafer inserter 232 along the track 244.

A wafer inserter configured for deployed wafer columns in opposite directions is depicted in FIG. 30. Two triggers, 211 and 213 are included in the handle 230 and are operatively coupled to upper and lower magazines of wafers 210 and 209, respectively. The upper trigger 211 inserts a wafer at the bottom of the top wafer column 212 and advances that column superiorly (in the positive Z-axis). The bottom trigger 213 inserts a wafer at the top of the lower wafer column and advances that column inferiorly (in the negative Z-axis). Alternatively, the wafer inserter could be designed so that one trigger could control both columns independently. Other configurations for deploying opposing wafer columns with a single wafer inserter may be used as would be obvious to a person skilled in the art.

Another possible wafer inserter embodiment includes a modular design, including a cartridge and track detachable from the handpiece. All the components may be disposable, or alternatively reusable, or some combination thereof. Such a design may simplify the use of multiple wafer sizes and configurations.

One method to deliver the wafers is through an inserter that guides the wafers into position and provides the force along the X-axis to slide one wafer under another and provide the lifting force across the height of the column to meet the surgical demands of the procedure. The inserter may be a fixed tip inserter but may also be a detachable tip inserter.

The fixed tip inserter provides a floor over which the wafers slide into position. The fixed tip references the distal tip of the wafer inserter track that directly supports the wafer column. A catch is designed at the distal end of the floor to hold the first wafer in place while the second wafer is inserted under the first. The second wafer elevates the first wafer and begins the wafer column. The second wafer is then held in place by the distal catch while the third wafer is inserted. The process is repeated until the desired column height is attained. The distal catch may engage the bottom wafer only or, optionally, may be configured to engage the bottom two or more wafers. If the sliding friction between the wafers results in an axial force that would advance the upper wafer while the lower wafer is inserted, having the catch engage the second wafer would prevent displacement of the upper wafer while building the column. However, if the friction is lower than the force to advance the upper wafer (i.e. the strength of the surrounding cancellous bone or tissue), then a shorter catch to engage only the bottom wafer would be adequate.

In the fixed-floor embodiment of the wafer inserter, wafers are inserted until the required height or force is attained. At that point, the distal catch is released. A longer plunger (removal plunger) may be used to remove the inserter. The removal plunger is placed along the track of the inserter and the inserter advance mechanism is used to push the inserter out of the vertebral body. The removal plunger pushes against the bottom wafer. The bottom wafer retains its position in the column within the vertebra and the reaction force forces the wafer inserter out from the vertebra. Similarly, the standard plunger may be designed with selectable travel. The plunger may be set to insert wafers, or to advance further and remove the wafer inserter. The height of the wafer column would be reduced by the thickness of the fixed tip, which preferably would be approximately 0.010" to 0.020" thick.

Figure 37:
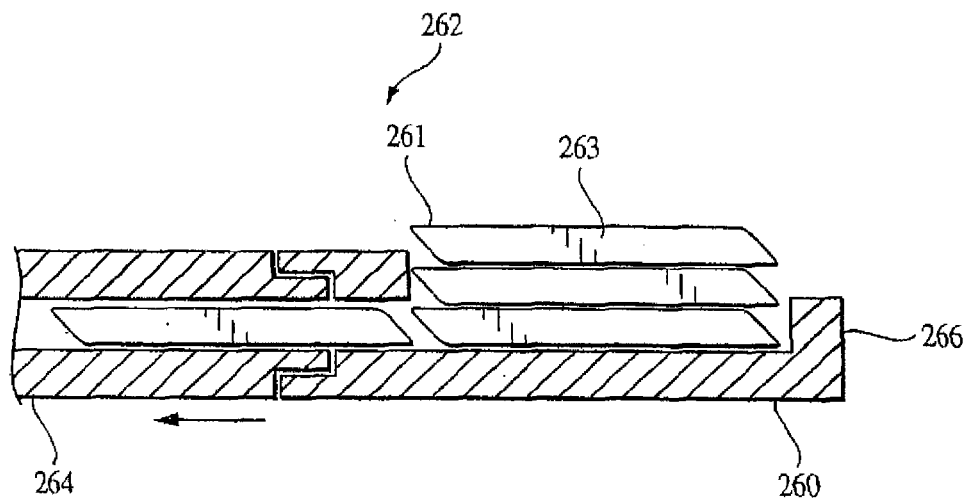
FIG. 37 shows a sectional view of a portion of an insertion device according to an alternate embodiment of the present invention.

The detachable tip wafer inserter embodiment, as seen in FIG. 37, includes a distal tip 260 of the wafer inserter 262 that is detachable from the main portion 264 of the inserter. One advantage provided by the detachable tip is that the height of the wafer column is not altered when the wafer inserter is removed. The tip 260 is preferably manufactured of the same material as the wafers. Thus, in a preferred embodiment, if the wafers are manufactured of PMMA, the distal tip 260 of the wafer inserter 262 is manufactured of PMMA. Alternately, the distal tip 260 may be manufactured of an implant grade metal or other medical grade implantable material. The distal tip 260 has a fixed distal shoulder 266 that holds the first wafer in place while the second wafer is inserted under the first. The height of the distal shoulder 266 may provide a stop for one wafer, or it may provide a stop for two or more wafers. The considerations applicable to the height of the distal catch apply to the height of the distal shoulder as well.

Figure 38:
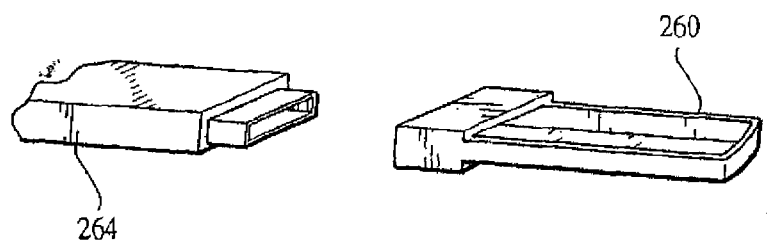
FIG. 38 shows a plan view of an alternate state of the insertion device of FIG. 37.

In the detachable tip embodiment, wafers are inserted until the desired height or force is attained. As seen in FIG. 38, the distal tip 260 is then released from the main portion 264 of the wafer inserter and the main portion 264 of the inserter is removed. The distal tip may be press-fit onto the track or may be bonded with an appropriate adhesive. In either case, the interface is designed to support the forces generated while building a wafer column, but shear when the extraction plunger is used to remove the wafer inserter. Optionally, the distal tip 260 may be keyed to interlock with the main portion 264 of the wafer inserter. For example, the main portion of the inserter may interlock with the distal tip by spring-loaded hooks that are mechanically compressed when the tip is to be released. Alternately, the hooks may be spring-loaded in the release position and mechanically expanded to engage the distal tip. In another embodiment, the detachable tip may be press-fit onto the wafer inserter or bonded with a weak adhesive. When the wafer inserter is to be removed, a force may be applied using a longer plunger or equivalent mechanism as in the fixed tip wafer inserter to dislodge the removable tip. The track of the wafer inserter may be then removed.

Both the fixed tip and detachable tip wafer inserters can be configured to deploy wafers in opposing columns. In such an embodiment, one column may be built in the positive Z-axis. Thus, if the supporting bone below the distal end of the track begins to yield, a second column in the negative Z-axis can be built by inserting wafers below the track. Once the negative Z-axis column has provided enough support for the wafer inserter, insertion of wafers into the positive Z-axis column can be resumed. The considerations applicable to distal stop or catch and material selection previously described also apply to the bi-directional wafer inserter. Reference is made to FIG. 30.

Figure 39:
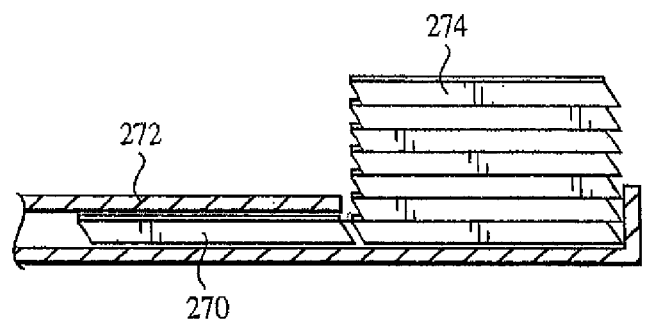
FIG. 39 shows a sectional view of an insertion device according to an embodiment of the present invention, configured to deploy distraction device similar to that depicted in FIGS. 31-33.
Figure 40:
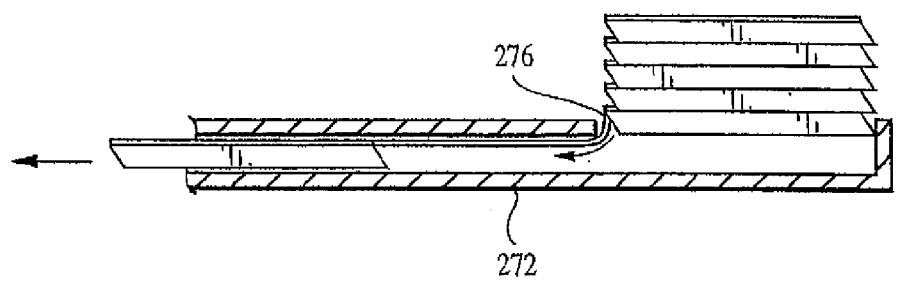
FIG. 40 shows a sectional view of an alternate state of the insertion device depicted in FIG. 39, configured for the removal of the distraction device similar to that depicted in FIGS. 31-33.

When inserting wafers connected via a tether, it is preferred to use the wafer inserter embodiment shown in FIG. 34 but the inserter may be either fixed tip or detachable tip. (A cross-sectional view of the track used to deploy tethered wafer is provided in FIG. 57). The wafers are stacked in a cartridge in the wafer inserter. To position the wafers, the wafers are advanced along the top of the plunger and the end most wafer is inserted at the bottom of the column. FIG. 39 shows the wafers 270 in the wafer inserter 272 being inserted into the surgical site. In order to remove the column 274, the bottom most wafer is removed first. In FIG. 40, the entry port at the distal tip 276 of the wafer inserter 272 provides a fulcrum over which the tether slides. This ensures that subsequent wafers are pulled down, then out of the wafer inserter track without twisting relative to the track.

A number of options relating to both the wafer inserter and the wafers are available. FIGS. 41-45 show wafers 280 having squared ends 282 being inserted with a wafer inserter that lifts the leading wafer. When the track 284 of the wafer inserter is placed in the prepared channel in the surgical site, the wafer elevator 286 is in its down position, as seen in FIG. 41. A force (F1) is applied to the wafers in the delivery channel of the wafer inserter. FIG. 42 shows the first wafer 288 advancing past the wafer elevator 286. The wafer elevator 286 flexes to allow the wafer 288 to pass into the lifting section of the wafer inserter. The wafer 288 then proceeds to the distal stop 290 of the wafer inserter track 288, as seen in FIG. 43. The wafer elevator 286 is drawn back slightly to clear the inserted wafer 288. As seen in FIG. 44, the elevator 286 is then advanced (F2) to engage the bottom surface 292 of the newly inserted wafer 288. A force (F3) is applied to the wafer inserter to advance another wafer 294 under the inserted wafer 288. As the wafer 294 is inserted it pushes the wafer elevator 286 to engage the wafer 288 or column of wafers previous inserted and elevates the proximal end 296 of the lower most wafer 288. The new wafer 294 is then inserted at the bottom of the column. FIG. 45 shows this process repeated with consecutive wafers to create a column as may be desired.

As seen in FIG. 46, an alternate embodiment of the wafer inserter involves a wafer inserter 300 designed for inserting curved wafers 302. There may be surgical or structural advantages to inserting wafers that are curved in a transverse plane. FIG. 46 also illustrates how a curved wafer 302 may better fit the anatomy of the vertebral body.

Curved wafers may be inserted using either embodiment of the previously described wafer inserters (fixed tip or detachable tip) by incorporating a curved wafer track. The wafer and track are then configured to have a constant radius. The instruments to prepare the vertebra for the inserter are similar to the ones described for the straight inserter, but designed to function along a curve. The curve is set to approximately match the anterior curvature of the vertebral body and may be provided in a range of radii to accommodate patient size variation and variation in vertebral shape along the length of the spine. Alternatively, the curved wafer inserter can be configured to deploy wafers in opposing columns. The bi-directional deployment of wafers may be independent, enabling the physician to increase either column as needed, or wafer deployment may be linked, in which case a wafer would be inserted into each column simultaneously.

Distraction Device and Procedure Applied to Vertebral Compression Fractures

The ability to enter the vertebral body via an extrapedicular approach dramatically increases the cross sectional size available for placing a device into the vertebral body. Current extrapedicular surgical techniques use a 6 mm ID cannula. According to the present invention, a rectangular cannula of approximately 4 mm to 12 mm in width in a transverse plane and approximately 6 mm in height in a vertical plane can be placed into the lumbar and lower thoracic spine. Upper thoracic vertebrae, however, may be limited to a width of 3 mm to 8 mm in a transverse plane and a height of 3 mm to 6 mm in a vertical plane.

Figure 47:
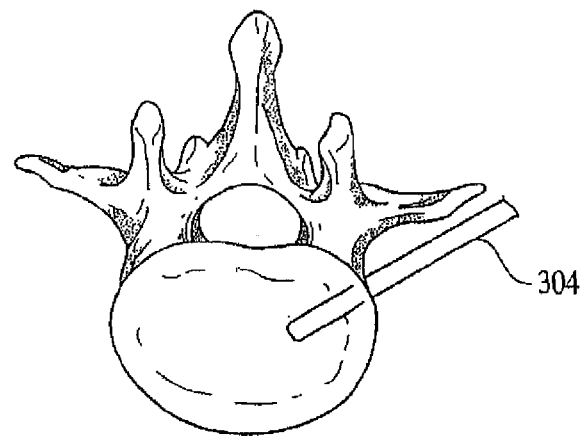
FIG. 47 depicts the implementation of a regimen for treatment of a vertebral compression according to an embodiment of the present invention, by plan view.
Figure 48:
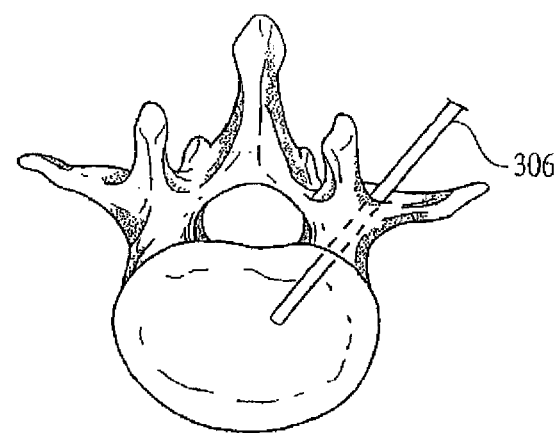
FIG. 48 depicts the implementation of a regimen for treatment of a vertebral compression according to an alternate embodiment of the present invention.

FIG. 47 illustrates an extrapedicular approach to a vertebral body wherein an access channel 304 is placed through the posterolateral wall of the vertebral body. Other approaches may optionally be used for placing the wafer inserter or inserters, although this may limit the access channel dimensions and corresponding implant size. FIG. 48 illustrates a transpedicular approach to the vertebral body wherein an access cannula 306 is placed through the pedicle. In the extrapedicular approach, cannulae may be placed bilaterally, through each pedicle. Similarly, two cannulae may be placed bilaterally using the extrapedicular approach, one on each side.

Figure 49:
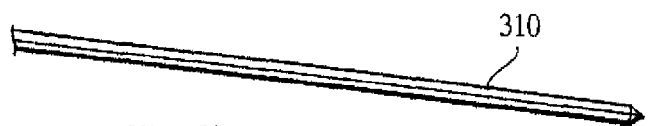
FIG. 49 shows a plan view of an apparatus for use in deploying the distraction device according to a further alternate embodiment of the present invention.
Figure 50:
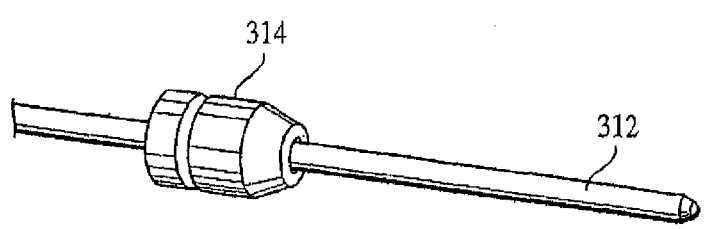
FIG. 50 shows a plan view of an apparatus for use in deploying the distraction device to be used in conjunction with the apparatus of FIG. 49.

A preferred procedure for placing the wafers involves placing a guide wire into the vertebral body via an extrapedicular approach under fluoroscopy. An example guide wire 310 is illustrated in FIG. 49. A cannulated tamp is placed over the guide wire and advanced to the vertebral cortical wall. In one embodiment, as seen in FIG. 50, the tamp 312 is cylindrical and is shown with a detachable handle 314. One method of advancing the tamp into the vertebra involves tapping the tamp with a hammer or pushing/twisting the tamp by hand. Preferably, tamp advancement is monitored with a fluoroscope to place the distal tip of the tamp past the midline and spanning the midsection or anterior aspect of the vertebral body. Ideally, the tamp references or is indexed to the guide wire to minimize advancement of the tamp beyond the length of the guide wire. After advancing the tamp through the vertebral body to its desired position, the tamp is removed and the guide wire is left in place.

Figure 51:
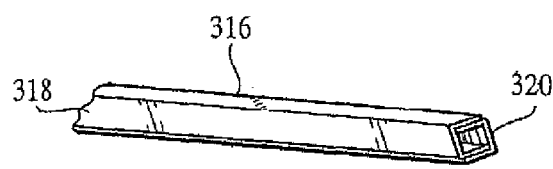
FIG. 51 shows a plan view of an apparatus according to an embodiment of the present invention.
Figure 52:
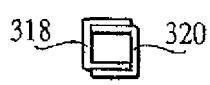
FIG. 52 shows an alternate plan view of the apparatus of FIG. 51.
Figure 53:
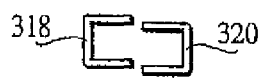
FIG. 53 shows a plan view of the apparatus of FIG. 52 according to an alternate state.

An expandable access channel is advanced over the guide wire into the vertebra through the opening created in the vertebral body. Again, the channel may reference the guide wire to prevent advancing the channel beyond the length of the guide wire. Expanding the channel permits adjustment of the channel to a size sufficient for receiving a wafer inserter. FIG. 51 shows one embodiment of the expandable access channel 316 where two channels 318 and 320 are placed together with their open surfaces facing one another. FIG. 52 shows the two channels 318 and 320 in a "closed" configuration, while FIG. 53 shows the two channels 318 and 320 in an open configuration. The closed expanding channel 316 is placed over the guide wire 310 and advanced into the vertebral body to the tip of the guide wire. The guide wire is removed. Position of the expanding channel and subsequent tapered and blunt expanders should be monitored via fluoroscope. While an expandable access channel is specifically discussed and contemplated, it is possible to use an access channel or series of channels which is not expandable and which is at its fullest dimension before advancement into the vertebra.

Figure 54:
FIG. 54 shows a plan view of an apparatus according to an embodiment of the present invention.
Figure 55:
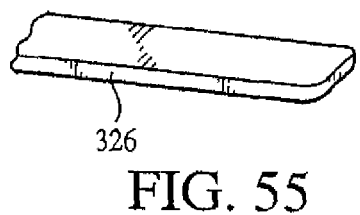
FIG. 55 shows a plan view of an alternate embodiment of the apparatus depicted in FIG. 54.

Once the expandable access channel is in place, the guide wire may be removed. With the expandable access channel in place, a mandrel is placed inside the channel. The mandrel should be larger than the collapsed channel in order to expand the channel as the mandrel is driven distally. As seen in FIG. 54, the mandrel 322 may have a tapered end 324 for ease of deployment. Optionally, the mandrel may have a shape corresponding with the shape of the access channel. Thus, when a rectangular access channel is employed, a rectangular mandrel may be used. Advancing the mandrel through the length of the access channel expands the open channels in a transverse plane creating a cavity in the vertebral body corresponding in shape to the shape of the expanded access channel. It is preferred that a second mandrel is provided with a blunt end in the event that the tapered end of the first mandrel does not fully expand the access channel. FIG. 55 depicts a blunt-end mandrel 326. In either case, the mandrel should reference the access channel to prevent advancement of the mandrel beyond the length of the channel. Optionally, a series of sequentially larger mandrels may be used to gradually enlarge the expanding channel. A hydraulic expansion device, or other suitable expansion device obvious to those skilled in the art, may alternately be used to enlarge the expanding channel.

In a first embodiment of the invention, the mandrel is removed from the expanded access channel and a wafer inserter is passed through the channel. The wafer inserter may be a track, preferably having a lip at its distal end for preventing the wafers from sliding too far into the vertebra, and is inserted within the access channel. The distal end of the wafer inserter placed in the surgical site may be set by a positive stop at the proximal or distal end of the expandable access channel, or visually using fluoroscope. FIG. 3 illustrates a wafer inserter track 64 in position in the vertebral body.

It is recommended to keep the access channel in position during the entire procedure. This will ensure minimal invasiveness of the procedure. Removal of the access channel risks inability to locate the channel already created.

The wafer inserter includes a plunger that slides within a track for advancing wafers down the track into the vertebral body. To position a wafer in the vertebral body, a wafer is placed in the track and the plunger is advanced to full forward position to place the wafer at the distal end of the track. To place a second wafer on the track, the plunger is retracted to the point where a second wafer drops from the cartridge of wafers to a position in front of the plunger. The plunger advances the wafer to slide the second wafer underneath the first wafer. The force applied to the trailing edge of the second wafer causes the first wafer to be raised.

Figure 56:
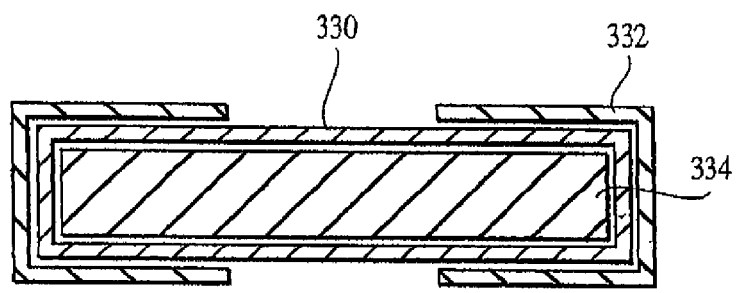
FIG. 56 shows a sectional view of an apparatus according to an embodiment of the present invention, suitable for deployment of distraction device similar to that depicted in FIGS. 31-33.

Various configurations of the wafer inserter and access channel are provided. As seen in FIG. 56, the wafer inserter track 330 passes through the expanded access channel 332. The track 330 is sized to permit only one wafer to pass there through. The plunger 334 is sized to fill the wafer inserter track's internal opening. Alternatively, the expandable access channel 332 may be interchanged with a non-expandable or fixed dimension access channel.

Figure 57:
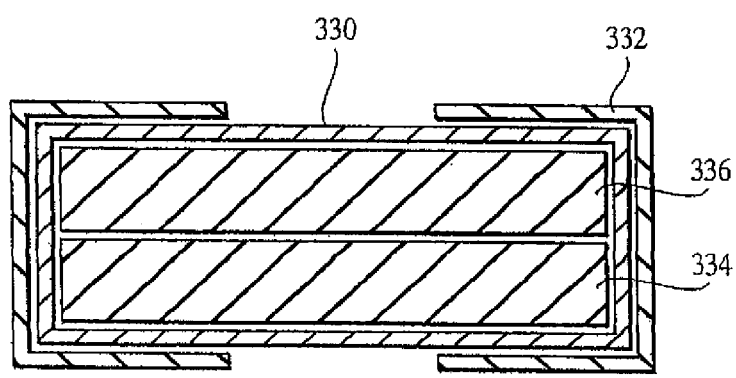
FIG. 57 shows a sectional view of an alternate configuration of the apparatus depicted in FIG. 56.

FIG. 57, shows a wafer inserter and access channel configuration wherein the wafer inserter track 330 is sized for accommodating the plunger 334 with a wafer 336 resting on top of the plunger 334. The wafers 336 are fed through the wafer track 330 on top of the plunger 334. When the plunger 334 is retracted the length of one wafer, a wafer drops down in front of the plunger. When the plunger is advanced, the wafer is then inserted under the column of wafers. Simultaneously, a wafer from the bottom of the column in the cartridge is advanced along the top of the plunger.

FIG. 37 shows a column 261 of wafers 263 being formed using a detachable tip wafer inserter 262, the tip 260 of which is detachable from the bulk of the wafer inserter 264. The process of inserting wafers is repeated with consecutive wafers until a column of sufficient height is created to restore the vertebral body height per physician discretion. During repetitions, vertebral body height and wafer position should be periodically checked via fluoroscope.

Alternately, a plurality of pre-stacked wafers may be inserted at once as a stack. Multiple wafers may be inserted simultaneously to vary the thickness added to the column in a single step, each stack of wafers thus acting as a single wafer insertable unit. Multiple wafers added may be of the same thickness or varying thicknesses. In this case, the wafer inserter would provide an option to select one, two, three or more wafers to be inserted simultaneously. Once selected, the wafer inserter feeds the stack of an appropriate number of wafers into the track and the stack is advanced into the wafer column. The wafer inserter elevates the preceding wafer to facilitate insertion of multiple wafers. Wafer stacks of any suitable size may be mixed to form a column in vivo.

If desired, the wafer inserter may be positioned intermediate to two inserted wafers. That is, the wafer inserter may be positioned along the wafer column. Thus, a subsequently deployed wafer would be inserted intermediate to previously inserted wafers. In this embodiment, the wafer inserter may be configured for insertion of the wafer in a vertical down direction, a vertical up direction, or any direction suitable for forming a column with the previously inserted wafers.

In the example of vertebral compression fracture reduction, the cancellous bone below the wafer inserter may not provide adequate support for the wafer column when reducing the proximal end plate. In such situations, it may be advantageous to deploy wafers proximally at the start while monitoring distal displacement of the wafer inserter. If the wafer inserter displaces distally, then wafers may be inserted distally to maintain the initial position of the wafer inserter.

Although the wafers may be straight or curved, straight wafers would likely provide the greatest surgical simplicity. Additionally, straight wafers more closely mimic current surgical techniques. However, a curved wafer requires a similar and only slightly modified technique of percutaneously placing a curved delivery instrument. The curved wafer offers an improved anatomic match between the wafer column and the anterior cortex of the vertebra, thereby increasing the surface area and available distraction force. Compression fractures typically involve collapse of the superior end plate in a generally flat fashion rotating about a coronal axis at the superior aspect of the posterior vertebral wall.

A curved wafer inserter may enable placement of the wafer more anterior in the vertebral body while increasing the implant surface area and associated distraction force. In vertebral compression fractures, the superior end plate is often displaced distally at an oblique angle about a coronal axis at the intersection of the superior end plate and the posterior wall of the vertebral body. This results in compaction of the anterior cortical wall and the underlying cancellous bone. Placing contoured wafers anteriorly to provide interior distraction that reduces the superior end plate would be advantageous; the wafer column would be positioned in a high weight bearing area of the vertebra.

When the fracture is reduced, or when the physician determines that an adequate number of wafers have been inserted, the wafer inserter may be removed with a removal plunger. The expanding access channel is left in place. Alternatively, if the distal tip of the wafer inserter is detachable, then upon removal of the wafer inserter, the tip is detached and remains inserted in the vertebral body as part of the column. Again, the expanding access channel is left in place.

After an adequate column of wafers is inserted, bone filler may be injected into the vertebra to encapsulate the wafers, provide weight bearing structure, and increase stability. The bone filler bonds the wafers to one another as well as to the filler mantle that interdigitates with the cancellous bone. The wafers may be solid in construction and thus require the filler to flow around the wafer column and bond to the outer surfaces of the wafers. Wafer-to-wafer bonding is then achieved through solvent activation of wafer interfaces via capillary effect. Alternately, the wafers may include tunnels to transport bone filler through the wafer column and out to the surrounding bone. Bone filler material would be injected into the wafer column and then flow through the column.

Figure 58:
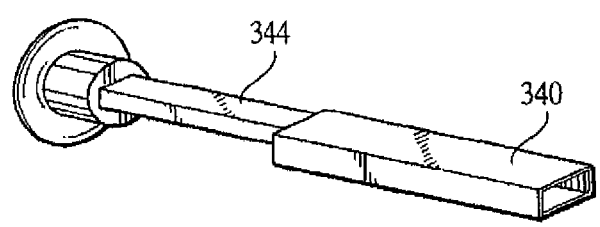
FIG. 58 shows a plan view of a bone filler insertion tool according to one embodiment of the present invention.

If bone filler is injected, an injection channel (340 of FIG. 58), which may prefilled with bone filler, is advanced along the channel into the vertebra. The bone filler should be allowed to thicken to the desired consistency before injection into the vertebral space. The injection is preferably completed under fluoroscopic observation to monitor bone filler flow. The total amount of filler injected is subject to physician judgment. The physician may elect to use additional injection channel(s).

Figure 59:
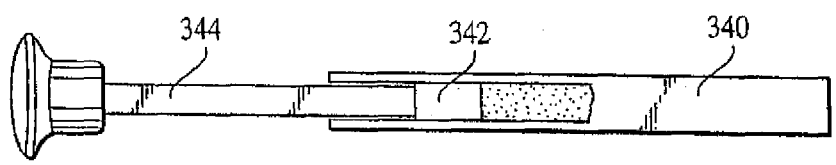
FIG. 59 shows a sectional view of the bone filler insertion tool depicted in FIG. 58.

If the introduction of bone filler is desirable, the injection channel may be passed through the expandable access channel. The injection channel is advanced until it approximates the wafer column. The injection channel includes a channel through which the bone filler flows, and a plunger to eject bone filler. FIG. 59 provides a cross-sectional view of the bone filler injection channel 340. The tip of the plunger 342 is of slightly larger cross-sectional area than the plunger 344. Thus, the plunger 344 is slightly smaller than the channel 340 and is easily inserted there through. The tip 342 is large enough to ensure complete coverage of the bone filler.

Once in position, the plunger on the bone filler delivery channel is advanced to inject the bone filling into and around the wafer column and the surrounding cancellous bone. In the event that bone filler from one delivery channel does not fill the vertebral body as per physician's discretion, then additional delivery channels can be filled with bone filler and bone filler delivered to the vertebral body in like fashion. Alternatively, any commercially available bone filler system may be used. Throughout the injection of bone filler, the vertebral body filling should be monitored under fluoroscopic guidance in order to avoid extravasation.

Typically, the physician will have more control over cement delivery and flow when the cement is delivered under low pressure. Delivering cement through larger cannula, either circular or rectangular in cross-section, will promote more uniform (laminar) flow at larger delivery pressures. The current preference is to deliver cement through a cylindrical tube. The present invention enables use of a channel with a significantly larger cross-sectional area. For example, the cross-sectional area of a 6 mm ID tube is 28 mm$^2$. A rectangular tube would enable up to a 6 mm vertical height and up to 12 mm in a transverse plane for a cross-sectional area of 82 mm$^2$. This provides a more than 150% increase in cross-sectional area.

The injection channel is left in place until the bone filler has thickened sufficiently that it will not flow out of the injection hole upon removal of the injection channel. The injection channel and the access channel are removed. Alternatively, the wafer inserter may remain in place and the bone filler may be injected through that device or the bone filler may be injected through any commercially available bone filler delivery system.

FIGS. 27 and 28 show two wafer column embodiments with cement interdigitation and with cancellous bone around the wafer columns. As seen in FIG. 28, the top and bottom wafers 198 and 200 respectively may be configured larger than the intermediate wafers 202 of the wafer column 192. This facilitates full encapsulation of the wafers by the bone filler. Bone cement fills the space left around the wafer column 192. Alternatively, as seen in FIG. 27, the wafers 194 of the wafer column 192 may be of constant size with bone cement filling the space surrounding the wafer column 192.

Another embodiment involves a wafer column built within a permeable membrane, the membrane having macro porosity. The membrane allows bone filler to flow through its wall into surrounding cancellous bone to provide better flow control, bone/filler interdigitation, stability, and structural support. Flow can thereby be controlled into surrounding cancellous bone as well as on and into the wafer column.

The Distraction Device Applied to Tibial Plateau Compression Fractures

The current invention also provides an instrument that can place wafers in a vertical column to reduce tibial plateau compression fractures through a minimally invasive approach. Thus, the implant simultaneously reduces the fracture and stabilizes the fracture.

In treating isolated compression fractures of one or both tibial condyles, a pathway to the underside of the depression is achieved by placing a guide wire percutaneously to a position that traverses the underside of the depression. The instrumentation for placing the implant is placed as described above in reference to vertebral compression. That is, a cylindrical tamp is advanced over the guide wire and then removed to allow an expandable channel to be placed and a wafer inserter positioned therein. Alternatively, a fixed dimension access channel may be used in place of the expandable channel.

Once in position, the wafer inserter places wafers in a vertical column under the compression fracture. The wafers are inserted until the articular surface is reduced (as confirmed by fluoroscopic or arthroscopic assessment). In treating an isolated tibial plateau compression fracture, the wafers may be used alone, or with an injectable bone filler material. The pathway through the tibial lateral wall may be filled with bone filler, or alternatively left to heal by natural bone. In cases where both a compression fracture and a splitting fracture are present, the splitting fracture may be reduced and stabilized by minimally invasive placement of one or more bone screws. After stabilizing the splitting fracture, the compression fracture can be reduced and stabilized as described for the isolated compression fracture.

Alternatively, removable wafers may be inserted under the compression fracture to reduce the fracture. Once reduced, the wafers are removed and the cavity created is filled with suitable bone filler material, or with wafers fabricated from allograft bone or other suitable bone substitute materials.

The Distraction Device Applied to Spinal Interbody Fusion

In performing spinal interbody fusion, the wafer inserter is placed through the annular wall from a posterior approach, or a posterior-lateral approach. At least four procedures are contemplated for performing spinal interbody fusion with the wafer device. These include a posterior approach, a posterior lateral approach, an anterior approach, and an extrapedicular approach.

Surgical Procedure—Posterior Approach

Figure 60:
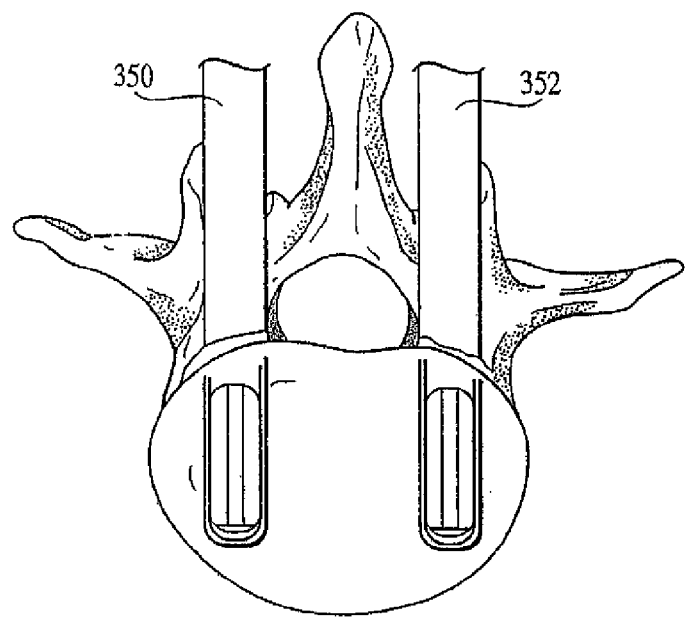
FIG. 60 depicts the implementation of a regimen for treatment of a vertebral body according to an embodiment of the present invention.

The posterior approach, as shown in FIG. 60, involves two columns of wafers each inserted lateral to a mid-sagittal plane. This is preferably done using two wafer inserters 350 and 352 allowing gradual distraction of the annulus in a parallel fashion. The wafer inserters may be equipped with load sensors to provide a digital readout of the load being applied by each column of wafers. This enables improved balancing of the distraction forces on each side of the annulus.

Surgical exposure is made to the posterior of the spine to access the posterior aspect of the annulus. Preferably, two openings are prepared in the annulus, each lateral to the mid-sagittal plane. The openings may be a straight-line incision, or a "C" shaped incision extending to the nucleus. The nucleus is then removed.

Bone spreaders/shavers are placed in the two openings and the vertebral bodies are distracted. The bone shaver or similar device is operated to remove the central portion of the annulus. A generally flat surface down to the bleeding bone of the superior and inferior endplates is prepared. The end plates are decorticated down to bleeding bone.

The prepared surface supports the wafer columns. A wafer inserter is placed in each opening and used in the manner described above. It is preferred to insert wafers in an alternating fashion between the two inserters to uniformly distract the annulus.

Annular tension is monitored as an indication of stability. When adequate stability is achieved as per physician discretion, no further wafers are inserted and the wafer inserters are removed. After removal, the incisions may be closed using standard techniques.

Surgical Procedure—Posterior-Lateral Approach

In the case of a posterior-lateral approach, one wafer inserter may be used with a wafer sized to cover the prepared endplates of opposing vertebral bodies.

A guide wire is percutaneously placed through the posterior-lateral surface of the annulus into the nucleus. An opening is prepared in the annulus by advancing a cylindrical cutter over the guide wire. An access channel is placed over the cutter and advanced to the annulus. Preferably, the access channel is then locked to the annulus and the guide wire and cutter are removed. The nucleus may then be extracted.

A bone spreader/shaver is placed through the access channel to distract the vertebral bodies. As in the posterior approach, the bone shaver or similar device is operated to remove the central portion of the annulus. A generally flat surface down to the bleeding bone of the superior and inferior endplates is prepared. The end plates are decorticated down to bleeding bone.

The prepared surface supports the wafer column. A wafer inserter is placed through the access channel and used in the manner described above to insert wafers and distract the adjacent vertebral bodies.

Annular tension is monitored as an indication of stability. When adequate stability is achieved as per physician discretion, no further wafers are inserted and the wafer inserters are removed. After removal, the incisions may be closed using standard techniques.

Surgical Procedure—Extra Pedicular Approach

A guide wire is percutaneously placed through the posterior-lateral wall of an adjacent vertebral body. The guide wire should be angled in a fashion to enter the nucleus. A cylindrical tamp is advanced to enlarge the opening. After the opening has been enlarged, an expanding access channel is placed over the tamp and advanced to the vertebral body. The access channel is locked to the vertebra and the guide wire and tamp are removed. The expanding access channel is enlarged to enable placement of a bone shaver and the wafer inserter. The nucleus may then be extracted.

As in the posterior-lateral approach, a bone spreader/shaver is placed through the access channel to distract the vertebral bodies. The bone shaver or similar device is operated to remove the disc's annulus. A generally flat surface down to the bleeding bone of the superior and inferior endplates is prepared. The end plates are decorticated down to bleeding bone.

Figure 61:
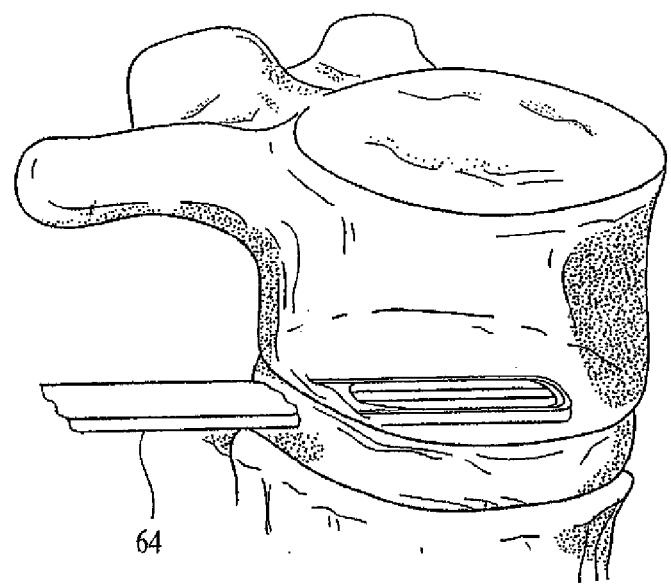
FIG. 61 depicts the deployment of an insertion device according to an embodiment of the present invention.

The prepared surface supports the wafer column. A wafer inserter is placed through the access channel and used in the manner described above to insert wafers and distract the adjacent vertebral bodies. FIG. 61 illustrates a wafer inserter 64 in position in a vertebral disc.

Annular tension is monitored as an indication of stability. When adequate stability is achieved as per physician discretion, no further wafers are inserted and the wafer inserters are removed. After removal, the incisions may be closed using standard techniques.

While a preferred embodiment of the present invention has been described, it should be understood that various changes, adaptation and modification may be made therein without departing from the spirit of the invention and the scope of the appended claims.

What is claimed is:

1. A curved expandable interbody fusion device for implantation into the intradiscal space between opposing vertebral bodies in a spine, comprising:
a curved elongate upper element including an outer surface for engaging a first vertebral body, a lower surface generally opposite said outer surface, a leading end and a trailing end, said curved elongate upper element being curved in a first plane;
a curved elongate lower element including an outer surface for engaging an opposing vertebral body, a leading end and a trailing end, said curved elongate lower element being curved in a second plane, said first plane and said second plane being generally parallel to each other, said upper element being movable in an expansion direction away from said lower element;
an elongate expansion member between said upper element and said lower element and movable along a path in a first direction that is substantially perpendicular to said expansion direction, said expansion member including a beveled lifting surface operable upon movement of said expansion member to engage the lower surface of said upper element to move said upper element away from said lower element in the expansion direction and expand said device, said first plane and said second plane being generally parallel to said first direction.

2. The device of claim 1, wherein said elongate expansion member has a leading end and a trailing end, said elongate expansion member being curved in a third plane between said leading end and said trailing end, said third plane being generally parallel to said first and second planes.

3. The device of claim 2, further comprising a cooperating constraint engageable upon slidable receipt of said expansion member between said upper element and said lower element to constrain relative movement between said upper element and said expansion member in a direction transverse to said first axial direction.

4. The device of claim 3, wherein said cooperating constraint comprises one of an elongate ridge or elongate groove on said lower surface of said upper element and a complementary elongate ridge or elongate groove on said expansion member, said complementary ridge and groove being engageable upon slidable receipt of said expansion member between said upper element and said lower element.

5. The device of claim 4, wherein said complementary ridge and groove define a dovetail configuration engageable upon slidable receipt of said expansion member between said upper element and said lower element.

6. The device of claim 3, wherein, said lower surface of said upper element includes a beveled surface.

7. The device of claim 6, wherein said expansion member includes thereon a second beveled surface axially spaced from said beveled lifting surface and a portion between and interconnecting said beveled lifting surface and said second beveled surface.

8. The device of claim 7, wherein said beveled lifting surface and said second beveled surface are inclined in the same direction along the first direction.

9. The device of claim 6, wherein a detent on one of said upper element or said expansion member defines a cylindrical projection along the axial direction and wherein the other of said upper element or said expansion member defines a cylindrical recess along the axial direction for slidable receipt of said cylindrical projection therein.

10. The device of claim 1, further comprising complementary detents on said upper element and said expansion member engageable upon slidable receipt of said expansion member between said upper element and said lower element to limit axial travel of said expansion member relative to said upper element.

\* \* \* \* \*